(12) United States Patent
Chmielewski et al.

(10) Patent No.: US 10,774,475 B2
(45) Date of Patent: Sep. 15, 2020

(54) BREATHABLE BACKSHEET, ABSORBENT ARTICLES, AND METHODS

(71) Applicant: ATTENDS HEALTHCARE PRODUCTS, INC., Greenville, SC (US)

(72) Inventors: Harry Chmielewski, Raleigh, NC (US); Edward Seames, Rock Hill, SC (US); Brian M. Spain, Marysville, MI (US)

(73) Assignee: ATTENDS HEALTHCARE PRODUCTS, INC., Greenville, NC (US)

( * ) Notice: Subject to any disclaimer, the term of this patent is extended or adjusted under 35 U.S.C. 154(b) by 438 days.

(21) Appl. No.: 15/177,086

(22) Filed: Jun. 8, 2016

(65) Prior Publication Data

US 2016/0354506 A1 Dec. 8, 2016

Related U.S. Application Data

(60) Provisional application No. 62/172,572, filed on Jun. 8, 2015.

(51) Int. Cl.
*A61F 13/514* (2006.01)
*B32B 5/26* (2006.01)
(Continued)

(52) U.S. Cl.
CPC ..... *D21H 27/002* (2013.01); *A61F 13/51405* (2013.01); *A61F 13/51458* (2013.01);
(Continued)

(58) Field of Classification Search
CPC .......... A61F 13/51405; A61F 13/51458; A61F 13/51478; B32B 2262/0253;
(Continued)

(56) References Cited

U.S. PATENT DOCUMENTS

| 3,881,489 A | 5/1975 | Hartwell ................ 128/287 |
| 4,588,457 A | 5/1986 | Crenshaw et al. ......... 156/62.8 |

(Continued)

FOREIGN PATENT DOCUMENTS

| CN | 104494245 A | 4/2015 |
| JP | 2015500056 | 1/2015 |

(Continued)

OTHER PUBLICATIONS

International Search Report and Written Opinion dated Sep. 1, 2016, for PCT/US2016/036476.

(Continued)

*Primary Examiner* — Elizabeth C Imani
(74) *Attorney, Agent, or Firm* — Norton Rose Fulbright US LLP

(57) ABSTRACT

The present disclosure includes cellulosic fiber barrier layer having a hydrophobic sizing to cause the barrier layer to exhibit hydrophobic properties. For example, the present cellulosic fiber barrier layers can be configured to have a high hydrostatic head (e.g., more than 200 mm $H_2O$) while retaining a high air permeability (e.g., 0.5 $ft^3/min-ft^2$). The present disclosure also includes laminates (e.g., a breathable backsheet assembly) including one of the present cellulosic fiber barrier layers and a nonwoven support layer positioned beneath and coupled (e.g., bonded) to the barrier layer, such that the laminate is configured to exhibit desirable liquid-barrier performance (e.g., pinhole-free performance at 400 mm $H_2O$ for 10 minutes, and/or the like). The present disclosure also includes disposable absorbent garments including at least one of the present cellulosic fiber layers and laminates (e.g., including one of the present laminates as a backsheet for the disposable absorbent garment).

21 Claims, 7 Drawing Sheets

(51) Int. Cl.
  *B32B 5/02* (2006.01)
  *B32B 29/00* (2006.01)
  *B32B 29/06* (2006.01)
  *B32B 7/12* (2006.01)
  *B32B 7/02* (2019.01)
  *B32B 7/04* (2019.01)
  *B32B 29/08* (2006.01)
  *B32B 29/02* (2006.01)
  *D21H 27/00* (2006.01)
  *D21H 11/04* (2006.01)
  *D21H 27/30* (2006.01)
  *D21H 21/16* (2006.01)

(52) U.S. Cl.
  CPC ........ *A61F 13/51478* (2013.01); *B32B 5/022* (2013.01); *B32B 5/26* (2013.01); *B32B 7/02* (2013.01); *B32B 7/04* (2013.01); *B32B 7/12* (2013.01); *B32B 29/005* (2013.01); *B32B 29/02* (2013.01); *B32B 29/06* (2013.01); *B32B 29/08* (2013.01); *D21H 11/04* (2013.01); *D21H 21/16* (2013.01); *D21H 27/30* (2013.01); *B32B 2262/0253* (2013.01); *B32B 2262/0276* (2013.01); *B32B 2262/062* (2013.01); *B32B 2262/14* (2013.01); *B32B 2307/54* (2013.01); *B32B 2307/581* (2013.01); *B32B 2307/718* (2013.01); *B32B 2307/726* (2013.01); *B32B 2307/7265* (2013.01); *B32B 2307/73* (2013.01); *B32B 2307/732* (2013.01); *B32B 2555/00* (2013.01); *B32B 2555/02* (2013.01)

(58) Field of Classification Search
  CPC ...... B32B 2262/0276; B32B 2262/062; B32B 2262/14; B32B 2307/54; B32B 2307/581; B32B 2307/718; B32B 2307/726; B32B 2307/7265; B32B 2307/73; B32B 2307/732; B32B 2555/00; B32B 2555/02; B32B 29/005; B32B 29/02; B32B 29/06; B32B 29/08; B32B 5/022; B32B 5/26; B32B 7/02; B32B 7/04; B32B 7/12; D21H 11/04; D21H 21/16; D21H 27/002; D21H 27/30
  See application file for complete search history.

(56) References Cited

U.S. PATENT DOCUMENTS

| | | | |
|---|---|---|---|
| 5,695,376 A | 12/1997 | Datta et al. | |
| 5,885,909 A | 5/1999 | Rudisill et al. | 442/82 |
| 6,207,258 B1 | 3/2001 | Varnell | 428/195 |
| 6,716,204 B1 | 4/2004 | D'Acchioli et al. | 604/385.19 |
| 7,195,621 B2 | 3/2007 | Ohnishi et al. | 604/385.23 |
| 2001/0025164 A1 | 9/2001 | Krautkramer et al. | 604/385.21 |
| 2004/0019340 A1 | 1/2004 | McBride | 604/378 |
| 2005/0245159 A1 | 11/2005 | Chmielewski et al. | 442/268 |
| 2009/0042468 A1 | 2/2009 | Suzuki et al. | 442/76 |
| 2011/0250816 A1 | 10/2011 | Fujiwara et al. | |

FOREIGN PATENT DOCUMENTS

| | | |
|---|---|---|
| WO | WO 2007/100040 | 9/2007 |
| WO | WO 2013/081879 | 6/2013 |

OTHER PUBLICATIONS

Notice of Reasons for Rejection issued in corresponding Japanese Patent Application No. 2017-564551 dated Jun. 29, 2020 (English Translation Provided).

Cairpad® – 42 only

| Sample | Modified Pinhole (Soft/Soft) Test | | | Modified Pinhole (Soft/Hard) Test | | | Modified Pinhole (Hard/Hard) Test | | | Hydrohead |
|---|---|---|---|---|---|---|---|---|---|---|
| | 400 mm | 600 mm | 800 mm | 400 mm | 600 mm | 800 mm | 400 mm | 600 mm | 800 mm | |
| 1A | 0 | 0 | CS | CS | | | | | | 15 ± 2 mm H$_2$O |
| 1B | 0 | CS | | CS | | | | | | |
| 2A | 4P | | | CS | | | | | | |
| 2B | CS | | | CS | | | | | | |

Prototype 1 – 10/17/42

| Sample | Modified Pinhole (Soft/Soft) Test | | | Modified Pinhole (Soft/Hard) Test | | | Modified Pinhole (Hard/Hard) Test | | | Hydrohead |
|---|---|---|---|---|---|---|---|---|---|---|
| | 400 mm | 600 mm | 800 mm | 400 mm | 600 mm | 800 mm | 400 mm | 600 mm | 800 mm | |
| 1A | 0 | 0 | 0 | CS | | | CS | | | 199 ± 10 mm H$_2$O |
| 1B | 0 | 0 | 0 | 0 | 3P | | CS | | | |
| 2A | 0 | 0 | 0 | 1P | CS | | CS | | | |
| 2B | 0 | 0 | 0 | 0 | 2P | | CS | | | |

Prototype 2 – 10/36/42

| Sample | Modified Pinhole (Soft/Soft) Test | | | Modified Pinhole (Soft/Hard) Test | | | Modified Pinhole (Hard/Hard) Test | | | Hydrohead |
|---|---|---|---|---|---|---|---|---|---|---|
| | 400 mm | 600 mm | 800 mm | 400 mm | 600 mm | 800 mm | 400 mm | 600 mm | 800 mm | |
| 1A | 0 | 0 | 0 | 0 | 0 | 0 | CS | | | 461 ± 7 mm H$_2$O |
| 1B | 0 | 0 | 0 | 0 | 9P | CS | CS | | | |
| 2A | 0 | 0 | 0 | 3P | CS | | CS | | | |
| 2B | 0 | 0 | 0 | 0 | 0 | 3P | CS | | | |

Poly version – poly/42

| Sample | Modified Pinhole (Soft/Soft) Test | | | Modified Pinhole (Soft/Hard) Test | | | Modified Pinhole (Hard/Hard) Test | | | Hydrohead |
|---|---|---|---|---|---|---|---|---|---|---|
| | 400 mm | 600 mm | 800 mm | 400 mm | 600 mm | 800 mm | 400 mm | 600 mm | 800 mm | |
| 1A | 0 | 0 | 0 | 0 | 0 | 0 | 0 | 0 | 5P | High |
| 1B | 0 | 0 | 0 | 0 | 0 | 0 | 0 | 5P | | |
| 2A | 0 | 0 | 0 | 0 | 0 | 0 | 0 | 1P | | |
| 2B | 0 | 0 | 0 | 0 | 0 | 0 | 1P | | | |

FIG. 5

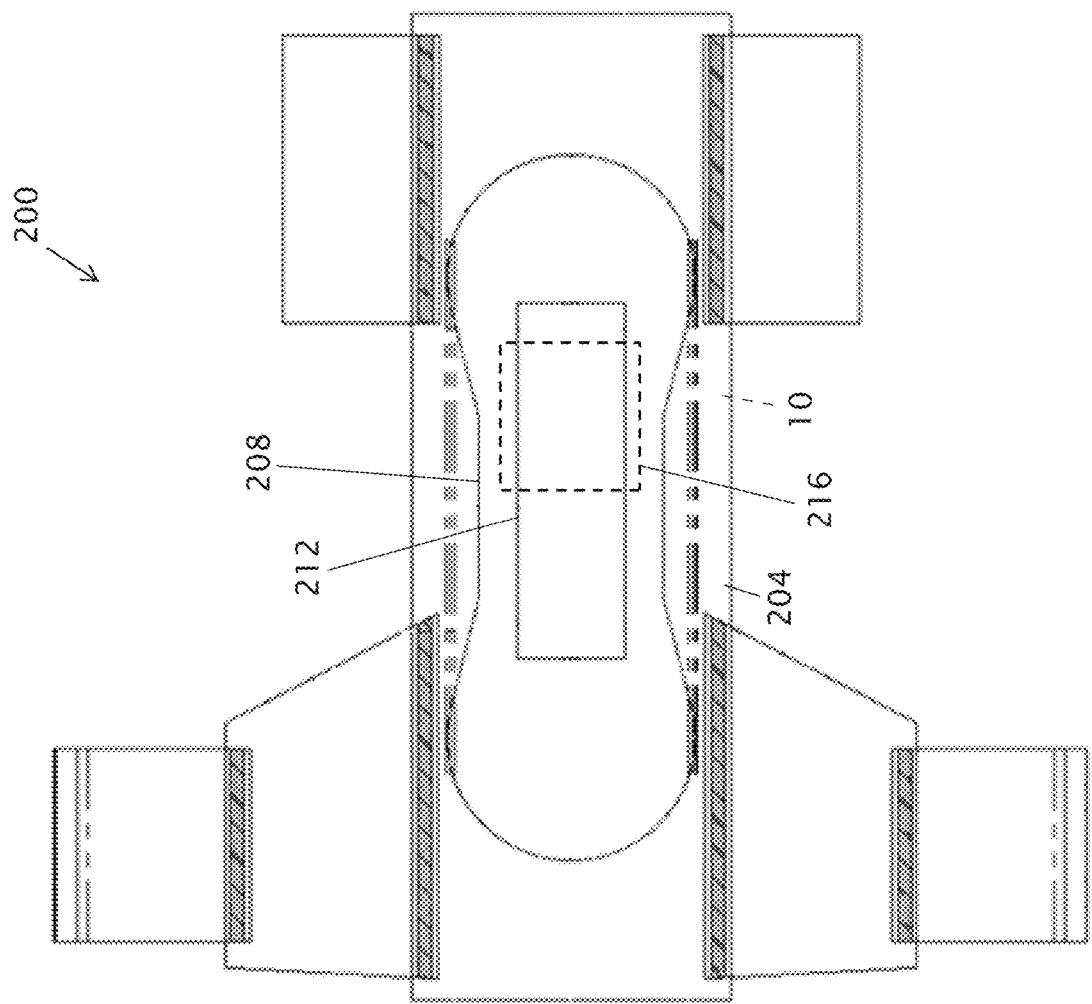
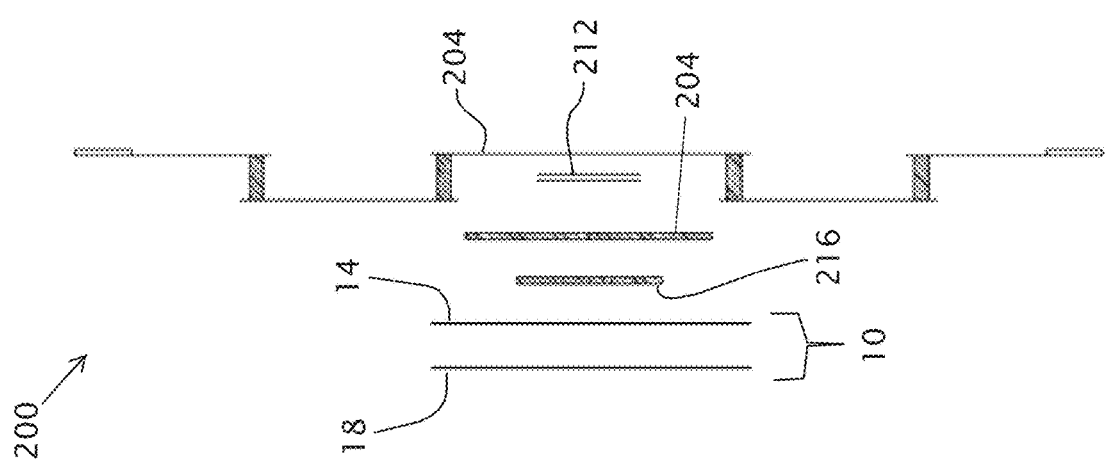

BREATHABLE BACKSHEET, ABSORBENT ARTICLES, AND METHODS

CROSS-REFERENCE TO RELATED APPLICATIONS

This application claims priority to U.S. Provisional Application No. 62/172,572 filed Jun. 8, 2015, which application is incorporated by reference in its entirety.

FIELD OF INVENTION

The present invention relates generally to cellulosic fiber barrier material that is air-permeable and liquid-impermeable; and, more particularly, but not by way of limitation, to laminates that exhibit both reliable liquid barrier performance and high air permeability for use in disposable absorbent products such as infant diapers, adult incontinence briefs, pull-up underwear and bladder control pads, bed pads, feminine hygiene products, and surgical gowns, drapes, and masks.

BACKGROUND

Disposable absorbent products have met with widespread acceptance in the marketplace for a variety of applications, including infant and adult incontinence care, in view of the manner in which such products can provide effective and convenient liquid absorption and retention while maintaining a reasonable level of comfort for the wearer. However, a need exists for backsheet materials that can provide a level of air permeability more like that of a woven textile fabric of conventional clothing, while maintaining sufficient liquid barrier performance for its intended use. Absorbent products with an air permeable backsheet can provide increased comfort for the wearer by helping to maintain the natural transpiration of the skin to reduce heating and sweating of occluded sections of the body. So-called "breathable" backsheet films that are currently used in the hygiene industry allow for a slow diffusion of water molecules through them but provide negligible air permeability.

Liquid barrier performance of fabric and nonwovens adequate for certain end uses can be achieved with fibers that have advancing water contact angles of less than 90° if the nonwoven is comprised of small enough pores. For example, the meltblown component of a Spunbond-Meltblown-Spunbond (SMS) polypropylene nonwoven provides the small pores required to improve liquid barrier performance for leg gathers in a baby diaper. While the pores are small enough to provide some liquid barrier performance, they are still large enough to maintain a high level of air permeability. Recent attempts to further improve the liquid barrier performance of nonwovens, and to reduce the basis weight of the nonwoven required for performance, has focused on making the nonwovens with finer fibers that can generate even smaller pore size distributions. For example, U.S. Pat. No. 5,885,909, hereby incorporated by reference, teaches the use of sub-denier fibers for nonwoven structures to achieve high hydrostatic head with high air permeability. Another example, U.S. Pat. No. 7,195,621, hereby incorporated by reference, uses a meltblown nonwoven backsheet for a disposable garment to enhance breathability.

U.S. Patent Application Publication US 2005/0245159, hereby incorporated by reference, discloses a breathable barrier composite comprising a compressed mat of airlaid hydrophobic cellulose fibers and thermally-bonded poly-olefin fibers. However, it is not possible to generate a uniform distribution of small enough pores with this type of a fiber composite.

SUMMARY

This disclosure includes cellulosic fiber layers, such as paper or tissue, with hydrophobic sizing that imparts hydrophobic properties to the cellulosic fibers, which in the absence of the hydrophobic sizing might otherwise be expected to cause the cellulosic fiber layer to exhibit hydrophilic properties. The hydrophobic properties make the present cellulosic fiber layers suitable for use as barrier layers in various disposable absorbent articles such as, for example, infant diapers, adult incontinence briefs, pull-up underwear and bladder control pads, bed pads, feminine hygiene products, and surgical gowns, drapes, and masks. For example, such cellulosic barrier layers can be configured to exhibit low or desired liquid permeability while also exhibiting higher-than-expected levels of air permeability. A low or desired liquid permeability may, for example, be indicated by a minimum designated hydrostatic head. In some embodiments, the cellulosic fiber layer comprises a sheet of low-porosity cellulosic fiber material with, for example, a basis weight in the range of about 17-45 grams per square meter, which units can also be designated with gsm or $g/m^2$. In some embodiments, the present cellulosic fiber layers may be creped; for example, the present cellulosic fiber layers can comprise one or more sheets of creped paper or creped tissue.

This disclosure also includes multi-layered laminates and methods of manufacturing multi-layer laminates that comprise one of the present cellulosic barrier layers coupled to a support layer comprising a synthetic nonwoven. The present cellulosic barrier layers may, for example, be bonded directly or indirectly to the support layer, such as, for example, by one or more of: an adhesive, an ultrasonic bond, or other type of bond.

The present laminates can be configured to exhibit good or desirable liquid barrier performance. Good or desirable liquid barrier performance may, for example, by indicated by a laminate being configured to have a minimum designated hydrostatic head and/or to remain pinhole free under a designated hydrostatic head for a designated period of time. The present laminates can also be configured to exhibit higher-than-expected levels of air permeability. For example, the present laminates can be configured to provide both pinhole-free liquid barrier performance, and air permeability comparable to that of a polyester/cotton fabric. These properties make embodiments of the present laminates suitable and desirable for use as a breathable backsheet in place of less-breathable or non-breathable backsheet materials, such as poly films, that are often used as backsheet materials in disposable absorbent products. When the present laminates are used in or incorporated into such disposable absorbent products that include an absorbent core, the support layer typically faces away from the core, and the cellulosic barrier layer typically faces the core and is also closer to a wearer's skin during use, such that the upper or inner cellulosic barrier layer improves breathability relative to a traditional poly film, while the lower or outer support layer provides structural support and additional protection against leakage of liquids.

At least some embodiments of the present laminates also exhibit mechanical properties, such as tensile strength in the machine direction and/or cross direction, that enable the use of lower basis weight nonwovens in the laminate than are traditionally used for backsheets. For example, the support layer of the present laminates can comprise a nonwoven material with a basis weight as low as 17 gsm, which is lower than typically used for nonwoven backsheets, while still exhibiting sufficient mechanical integrity during use. In some embodiments, the support layer comprises a sheet of high-hydrohead SMS nonwoven material with a basis weight of about 17-42 gsm.

In some embodiments, the hydrophobic sizing is incorporated into the cellulosic fiber layer alone prior to coupling the cellulosic barrier layer to the nonwoven support layer. For example, a sizing agent can be added to a pulp slurry prior to forming the sheet of cellulosic fiber material, or can be applied in a finishing step, for example in a size press or coater, after drying of the formed sheet of cellulosic fiber material but prior to lamination to the nonwoven. In embodiments in which the hydrophobic sizing is added before the cellulosic barrier layer is coupled to the support layer, the laminate may include only two layers: the cellulosic barrier layer and the nonwoven support layer. While hydrophobic papers are produced for other applications, such hydrophobic papers, whether creped or uncreped, are not believed to have previously been laminated with nonwovens for use as barrier layers in absorbent products.

In other embodiments, the hydrophobic sizing is incorporated into the cellulosic barrier layer after the cellulosic barrier layer has been coupled to the support layer. For example, the laminate may be finished with an aqueous solution of sizing agent and dried to render the cellulosic barrier layer hydrophobic. Alkylketene dimer (AKD) is one example of such a sizing agent. In embodiments in which the hydrophobic sizing is added after the cellulosic barrier layer is coupled to the support layer, the laminate may include a third layer configured to stabilize the cellulosic fiber during the sizing process. Such a stabilization layer may, for example, comprise a sheet of spunbond nonwoven material and/or may have a basis weight of about 8-12 gsm. In such embodiments, large-scale commercial production of these types of multi-layered laminate may involve a two-step process comprising lamination of the layers, followed by treatment with an aqueous solution, for example, in a size press for paper finishing or a padder for textile finishing. Lamination may, for example, be via an adhesive such as a filamentary adhesive or via thermal bonding. While each of these lamination and sizing processes is individually known in the art, these processes are not believed to have previously been used together to produce hydrophobic laminates. In some embodiments in which the hydrophobic sizing is added after lamination, the cellulosic fiber layer is creped and thus includes, for example, one or more layers of creped tissue. The fiber layer may be creped, for example, when each sheet is first formed via on-machine creping or after a sheet is formed via off-machine creping.

Some embodiments of the present breathable backsheet assemblies comprise: a cellulosic fiber barrier layer having a hydrophobic sizing, the barrier layer having an air permeability of more than 0.5 ft$^3$/min-ft$^2$ and configured to hold a hydrostatic head of more than 200 mm H$_2$O; and a support layer positioned beneath and coupled to the fiber layer, the support layer comprising a nonwoven fabric; where the barrier layer and support layer define a laminate.

In some embodiments of the present breathable backsheet assemblies, the laminate is configured to remain pinhole free at 400 mm H$_2$O for 10 minutes using the Liquid-Column Pinhole (Soft-Hard) Test Method.

In some embodiments of the present breathable backsheet assemblies, the barrier layer has a basis weight between 15 grams per square meter (gsm) and 45 gsm.

In some embodiments of the present breathable backsheet assemblies, the barrier layer comprises two sheets of cellulosic fiber material, each sheet having a basis weight of between 15 gsm and 20 gsm.

In some embodiments of the present breathable backsheet assemblies, the barrier layer is creped. In some such embodiments, the barrier layer has a percent elongation of between 5% and 55%.

In some embodiments of the present breathable backsheet assemblies, the barrier layer is bonded to the support layer by a filamentary adhesive or thermal bonds.

In some embodiments of the present breathable backsheet assemblies, the support layer has a basis weight of no more than 20 gsm. In such embodiments, the support layer comprises a spunbond-meltblown-spunbond (SMS) nonwoven configured to hold a hydrostatic head of more than 150 mm H$_2$O.

Some embodiments of the present disposable absorbent articles comprise: an embodiment of the present breathable backsheet assemblies; a liquid-permeable topsheet; and an absorbent core positioned between the topsheet and the breathable backsheet assembly, the absorbent core comprising cellulosic fibrous material and/or superabsorbent polymeric (SAP) particles; where the breathable backsheet assembly is coupled to the topsheet.

In some embodiments of the present disposable absorbent articles, the absorbent article is configured to not substantially reduce the surface tension of saline or urine passing through the topsheet to the barrier layer. In some such embodiments, the absorbent article further comprises: an acquisition-distribution layer (ADL) disposed between the absorbent core and the topsheet, the ADL configured to not substantially reduce the surface tension of saline or urine passing through the ADL to the barrier layer.

Some embodiments of the present disposable absorbent articles further comprise: a compressible layer comprising a sheet of material having a thickness and that is compressible in a direction of its thickness; where the compressible layer is disposed between the barrier layer and the core, or between the barrier layer and the support layer. In some such embodiments, the compressible layer is not coextensive with the breathable backsheet assembly.

In some embodiments of the present disposable absorbent articles, the article comprises an incontinence brief, the barrier layer has an air permeability of more than 0.5 ft$^3$/min-ft$^2$ and is configured to hold a hydrostatic head of more than 600 mm H$_2$O, and the laminate is configured to remain pinhole free at 800 mm H$_2$O for 10 minutes using the Liquid-Column Pinhole (Soft-Hard) Test Method.

In some embodiments of the present disposable absorbent articles, the article comprises a pull-up underwear or a bladder control pad, the barrier layer has an air permeability of more than 1.5 ft$^3$/min-ft$^2$ and is configured to hold a hydrostatic head of more than 400 mm H$_2$O, and the laminate is configured to remain pinhole free at 600 mm H$_2$O for 10 minutes using the Liquid-Column Pinhole (Soft-Hard) Test Method.

In some embodiments of the present disposable absorbent articles, the article comprises a bedpad, the barrier layer has an air permeability of more than 1.5 ft$^3$/min-ft$^2$ and is configured to hold a hydrostatic head of more than 400 mm H$_2$O, and the laminate is configured to remain pinhole free at 400 mm H$_2$O for 10 minutes using the Liquid-Column Pinhole (Soft-Hard) Test Method.

Some embodiments of the present disposable absorbent articles further comprise: a spacer layer disposed between the barrier layer and the support layer, the spacer layer including a plurality of voids or interstices in at least a surface of the spacer layer that faces the barrier layer. In some such embodiments, the spacer layer is not coextensive with the breathable backsheet assembly.

In some embodiments of the present methods of making a disposable absorbent product, the method comprises: providing a liquid permeable topsheet, an absorbent core, a nonwoven support layer, and a cellulosic fiber layer having a hydrophobic sizing; and coupling the topsheet, barrier layer, and support layer together such that the absorbent core is retained between the topsheet and the barrier layer, and the barrier layer is retained between the core and the support layer.

Some embodiments of the present methods further comprise: providing an acquisition-distribution layer (ADL); and coupling the ADL to the topsheet such that the ADL is retained between the topsheet and the absorbent core.

In some embodiments of the present methods, the topsheet and ADL are configured to not substantially reduce the surface tension of saline or urine passing through the topsheet and ADL to the barrier layer.

"Superabsorbent" or "superabsorbent material" or "SAP" refers to a water-swellable, water-insoluble organic or inorganic material capable, under the most favorable conditions, of absorbing at least about 15 times its weight and, more desirably, at least about 30 times its weight in an aqueous solution containing 0.9 weight percent sodium chloride. The SAP materials can be natural, synthetic and modified natural polymers and materials. In addition, the SAP materials can be inorganic materials, such as silica gels, or organic compounds such as cross linked polymers.

"Disposable" refers to articles which are designed to be discarded after a limited use rather than being laundered or otherwise restored for reuse.

"Absorbent core" means a structure typically disposed between a topsheet and backsheet of an absorbent article and containing materials like SAP and/or cellulosic fibers that are configured to absorb liquid in the absorbent article. The absorbent core may also include a cover layer or envelope material. The cover layer or envelope may comprise; nonwovens, SAP, cellulosic or non-cellulosic materials, films, fibers or substrate made of any one two or all of these combination materials.

"Layer" when used in the singular can be a single element or a plurality of elements. For example, a plurality of sheets may together define a single layer, such as, for example, a layer with a particular function to which the sheets of the layer contribute.

"Nonwoven" fabrics, according to an INDA definition, are broadly defined as sheet or web structures bonded together by entangling fiber or filaments mechanically, thermally, or chemically. They are flat, porous sheets that are made directly from separate fibers or from molten plastic or plastic film. They are not made by weaving or knitting and do not require converting the fibers to yarn. The basis weight of nonwoven fabrics is usually expressed as gsm or grams per square meter.

"Nonwoven backsheet" is a backing substrate layer in the outer cover. The nonwoven backsheet is most often a nonwoven layer facing away from the wearer.

"Film" means a membrane-like layer of material formed of one or more polymers, which does not have a form consisting predominately of a web-like structure of fibers and/or other fibers. Film referred to in this disclosure as "poly film" is a film that is disposed in the outer cover laminate. Poly film can be breathable film or non-breathable.

"Liquid impermeable," when used in describing a layer or multi-layer laminate, means that a liquid, such as urine, will not pass through the layer or laminate, under ordinary use conditions, in a direction generally perpendicular to the plane of the layer or laminate at the point of liquid contact.

"Lamination" is the technique of manufacturing a material in multiple layers, so that the composite material has benefits of all the combined layers, such as, for example, improved mechanical strength or durability, improved stability, lower permeability to water, and/or other properties. A laminate is a permanently assembled object by heat, pressure, welding, or adhesives.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Machine direction" or "MD," with respect to the making of a nonwoven web material, refers to the direction along the material or laminate substantially parallel to the direction of forward travel of the material or laminate through the manufacturing line in which the material or laminate is manufactured. "Cross direction" or "CD," with respect to the making of a nonwoven or laminate, refers to the direction along the material substantially perpendicular to the direction of forward travel of the material through the manufacturing line in which the material and/or article is manufactured. "Z-direction," means perpendicular to plane approximated by the web along machine and cross direction.

As used in this disclosure, a "filamentary adhesive" is an adhesive that is deposited in the form of filaments between two elements to be joined. Filamentary adhesives can include, for example, hot-melt thermoplastic adhesives. In contrast to other types of adhesives that may be sprayed in a relatively uniform layer over a surface to be joined, a filament of filamentary adhesive is elongated and deposited along a discrete path, such that laminating two layers with filamentary adhesive will typically bond the two layers while leaving areas between filaments without adhesive, for example, such that the performance of the layers in adhesive-free areas is not affected by or subject to changes that an adhesive might otherwise impart, for example, by filling or covering pores. Examples of equipment for applying filamentary adhesive include, for example, UFD Fiberized Spray technology available from ITW Dynatech, Control Coat Applicator available from Nordson, as well as equipment from other suppliers.

The term "coupled" is defined as connected, although not necessarily directly, and not necessarily mechanically; two items that are "coupled" may be unitary with each other. The terms "a" and "an" are defined as one or more unless this disclosure explicitly requires otherwise. The term "substantially" is defined as largely but not necessarily wholly what is specified—and includes what is specified; e.g., substantially 90 degrees includes 90 degrees and substantially parallel includes parallel—as understood by a person of ordinary skill in the art. In any disclosed embodiment, the term "substantially" may be substituted with "within [a percentage] of" what is specified, where the percentage includes 0.1, 1, 5, and 10 percent.

Further, a device or system that is configured in a certain way is configured in at least that way, but it can also be configured in other ways than those specifically described.

The terms "comprise" and any form of thereof such as "comprises" and "comprising," "have" and any form thereof such as "has" and "having," and "include" and any form thereof such as "includes" and "including" are open-ended linking verbs. As a result, an apparatus that "comprises," "has," or "includes" one or more elements possesses those one or more elements, but is not limited to possessing only those elements. Likewise, a method that "comprises," "has," or "includes" one or more steps possesses those one or more steps, but is not limited to possessing only those one or more steps.

Any embodiment of any of the apparatuses, systems, and methods can consist of or consist essentially of—rather than comprise/include/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

Some details associated with the embodiments described above and others are described below.

BRIEF DESCRIPTION OF THE DRAWINGS

FIG. 5 depicts tables showing variations in pinhole test performance of prototype bedpads including embodiments of the present laminates or a commercial backsheet.

FIGS. 7A and 7B depict top and cross-sectional views, respectively, of another embodiment of the present disposable absorbent articles.

DETAILED DESCRIPTION OF ILLUSTRATIVE EMBODIMENTS

The present disclosure is directed to cellulosic fiber layers that have been treated with hydrophobic sizing to exhibit hydrophobic properties, and to multi-layer laminates that contain such a cellulosic fiber layer. Cellulosic fiber layers include primarily or entirely cellulose fibers. Examples of such cellulosic fiber layers include paper and tissue, such as, for example, low-porosity wetlaid tissue. In some embodiments, the cellulosic fiber layer is creped. The present laminates provide both high liquid barrier performance and high air permeability, and can be useful for absorbent hygiene products, bedpads, surgical gowns and drapes, and masks. As described in more detail below, it has been discovered that the fiber composition of the cellulose fiber sheet as well as physical properties of the sheet, including basis weight, elongation, can be selected to achieve a pore size distribution that can provide both high liquid hydrostatic head and high air permeability.

Figure 1A:
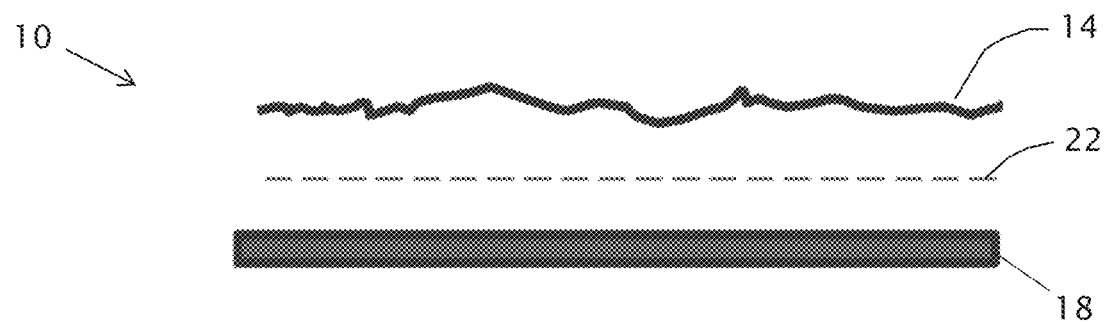
FIG. 1A depicts a diagrammatic, cross-sectional view of a first, 2-layer embodiment of the present laminates in which a lower one of the layers is suitable for use as the bottom backsheet nonwoven of an absorbent article.

Examples of the present laminates are depicted in FIGS. 1A, 1B, 1C, and 2. FIG. 1A depicts a first embodiment 10 of the present laminates that is suitable for use as a liquid barrier in at least some disposable absorbent articles. For example, laminate 10 may be used in place of a poly film or other type of barrier layer above a nonwoven backsheet, or in place of both a poly film barrier layer and nonwoven backsheet, in disposable absorbent articles. In the embodiment shown, laminate 10 comprises a cellulosic fiber layer 14 having a hydrophobic sizing that causes layer 14 to perform as a liquid barrier, and a support layer 18 coupled to the cellulosic barrier layer. In this embodiment, support layer 18 comprises a sheet of nonwoven fabric and is positioned beneath and bonded to barrier layer 14. In the embodiment shown, support layer 18 is bonded to barrier layer 14 via an adhesive 22 which may, for example, include a filamentary adhesive. As shown here, and described in more detail below, the combination of cellulosic barrier layer 14 and nonwoven support layer 18 define a laminate that is permeable to air and substantially impermeable to water. Laminate 10 may be described as a two-layer embodiment because it includes two primary functional layers, specifically, barrier layer 14 and support layer 18.

As used in this disclosure in the context of describing layers that are or are suitable for use in disposable articles, the terms "beneath," "above," "inward," and "outward" are used to describe a position of one layer relative to other layers or components, with a common reference point of a user of the absorbent article during use. For example, in the embodiment shown in FIG. 1A, barrier layer 14 is configured to be closer to a topsheet and closer to the absorbent core, support layer 18 is configured to be "beneath" and "outward" of the barrier layer because, when laminate 10 is incorporated into a disposable article as a backsheet or lower liquid barrier and the article is in use, support layer 18 is intended to be farther from the user than barrier layer 14. Similarly for this embodiment, barrier layer 14 is configured to be "above" and "inward" of the support layer because, when laminate 10 is incorporated into a disposable article as a backsheet or lower liquid barrier and the article is in use, barrier layer 14 is intended to be closer to the user than support layer 18.

Figure 1B:
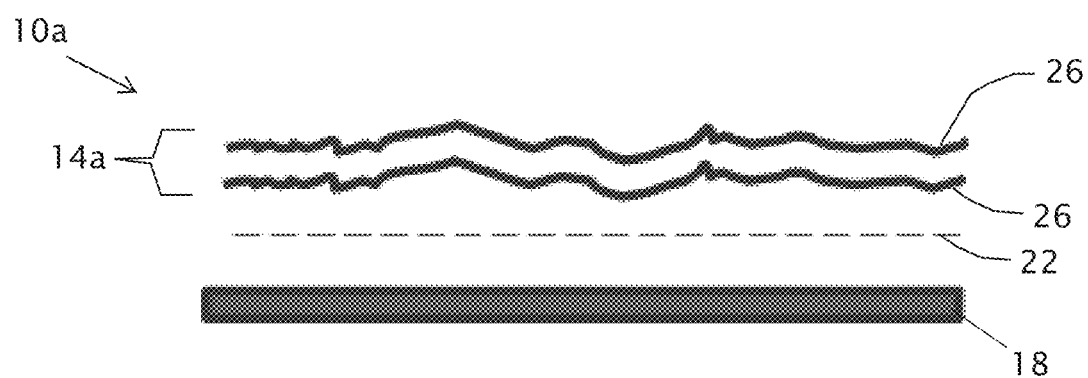
FIG. 1B depicts a diagrammatic, cross-sectional view of a second, 2-layer embodiment of the present laminates in which a lower one of the layers is suitable for use as the bottom backsheet nonwoven of an absorbent article.

FIG. 1B depicts a second embodiment 10a of the present laminates. Laminate 10a is structurally similar to laminate 10 in that laminate 10a also comprises a cellulosic barrier layer 14a having hydrophobic sizing, and a support layer 18 coupled to the fiber layer. However, laminate 10a differs from laminate 10 in that barrier layer 14a of laminate 10a comprises two sheets 26 of cellulosic fiber material, such as paper or tissue, that are coupled together. For example, in some embodiments, sheets 26 are bonded to one another via an adhesive such as a filamentary adhesive. As described above for barrier layer 14 of laminate 10, one or both of sheets 26 may be creped; for example, the present cellulosic fiber layers can comprise one or more sheets of creped paper or creped tissue. In this embodiment, sheets 26 can each have a lower basis weight than the single sheet of material defining support layer 14 in laminate 10 of FIG. 1A. For example, in some embodiments, sheets 26 can each have a basis weight of between 15 gsm and 20 gsm, such as, for example, a basis weight substantially equal to 17 gsm. As with laminate 10, laminate 10*a* may be described as a two-layer embodiment because it includes two primary functional layers, specifically, barrier layer 14*a* and support layer 18, with barrier layer 14*a* being defined by the combination of sheets 26.

In the embodiments of FIGS. 1A and 1B, and as described in more detail below, barrier layers 14 and 14*a* are defined by sheets of cellulosic fiber material in which the hydrophobic sizing is incorporated into the cellulosic fiber material alone, rather than being added after the barrier layer is coupled to support layer 18, and the sizing is therefore not also incorporated into the support layer 18. For example, a sizing agent can be added to a pulp slurry prior to forming the sheets of cellulosic fiber material. Alternatively, a sizing agent can be applied in a finishing step, such as in a size press or coater, after drying of the formed sheet of cellulosic fiber material, but either prior to coupling the layers, for example 14 and 18, together to define the laminate, or prior to coupling sheets, for example sheets 26, together to define the barrier layer, for example barrier layer 14*a*.

Figure 1C:
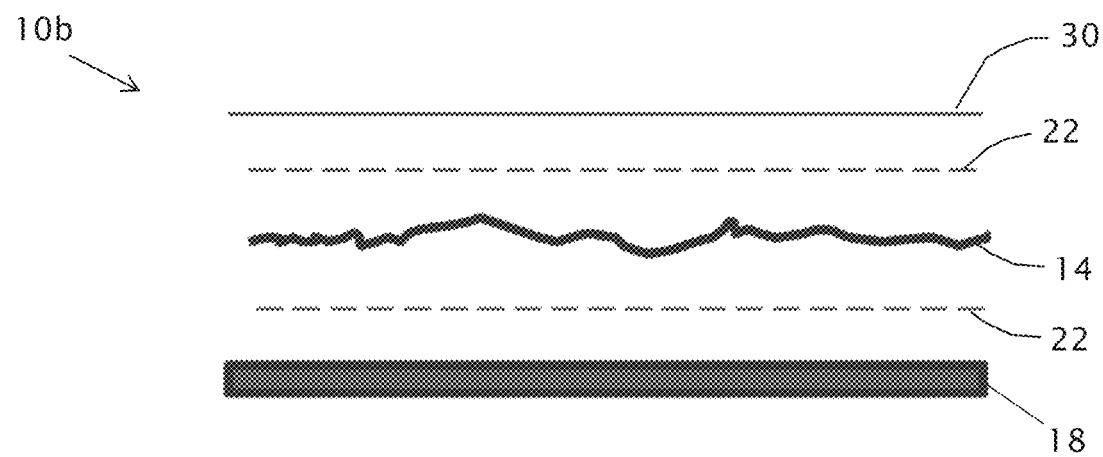
FIG. 1C depicts a diagrammatic, cross-sectional view of a third, 3-layer embodiment of the present laminates in which a lower one of the layers is suitable for use as the bottom backsheet nonwoven of an absorbent article.

FIG. 1C depicts a third embodiment 10*b* of the present laminates. Laminate 10*b* is structurally similar to laminate 10 in that laminate 10*b* also comprises a cellulosic barrier layer 14 having hydrophobic sizing, and a support layer 18 coupled to the barrier layer. However, laminate 10*b* differs from laminate 10 in that laminate 10*b* further comprises a nonwoven stabilization layer 30 disposed above and coupled to barrier layer 14. In the embodiment shown, stabilization layer 30 is bonded to barrier layer 14 via an adhesive 22, such as a filamentary adhesive. In contrast with laminates 10 and 10*a*, laminate 10*b* may be described as a three-layer embodiment because it includes three primary functional layers, specifically, barrier layer 14, support layer 18, and stabilization layer 30. While not shown in FIG. 1C, the fiber layer of laminate 10*b* can include two or more sheets 26 of cellulosic fiber material similar to what is shown for barrier layer 14*a* in FIG. 1B.

In the embodiments that include an upper stabilization layer 30 like the one shown in FIG. 1C, and as described in more detail below, the hydrophobic sizing can be incorporated into the cellulosic barrier layer after the cellulosic barrier layer has been coupled to the support layer. For example, the laminate may be finished with an aqueous solution of sizing agent, such as alkylketene dimer (AKD), and dried to render the cellulosic fiber layer hydrophobic. In embodiments in which the hydrophobic sizing is added after the cellulosic fiber layer is coupled to the support layer, the laminate may include a third layer configured to stabilize the cellulosic fiber during the sizing process. For example, in some embodiments, stabilization layer 30 comprises a sheet of unfinished spunbond nonwoven material with a basis weight of about 8-12 gsm.

Figure 2:
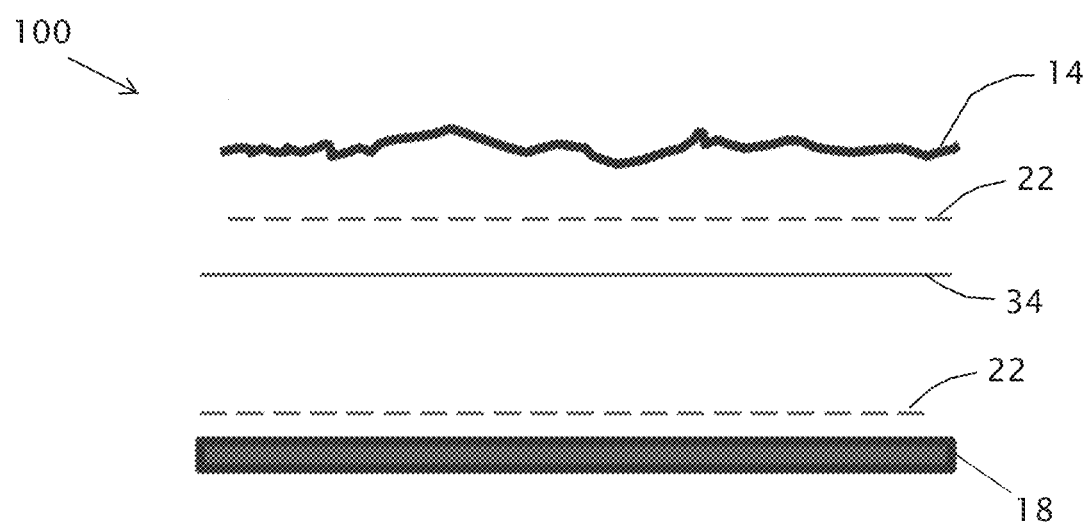
FIG. 2 depicts a diagrammatic, cross-sectional view of a fourth embodiment of the present laminates in which the laminate is used with or includes an additional bottom backsheet nonwoven in an absorbent article.
Figure 3:
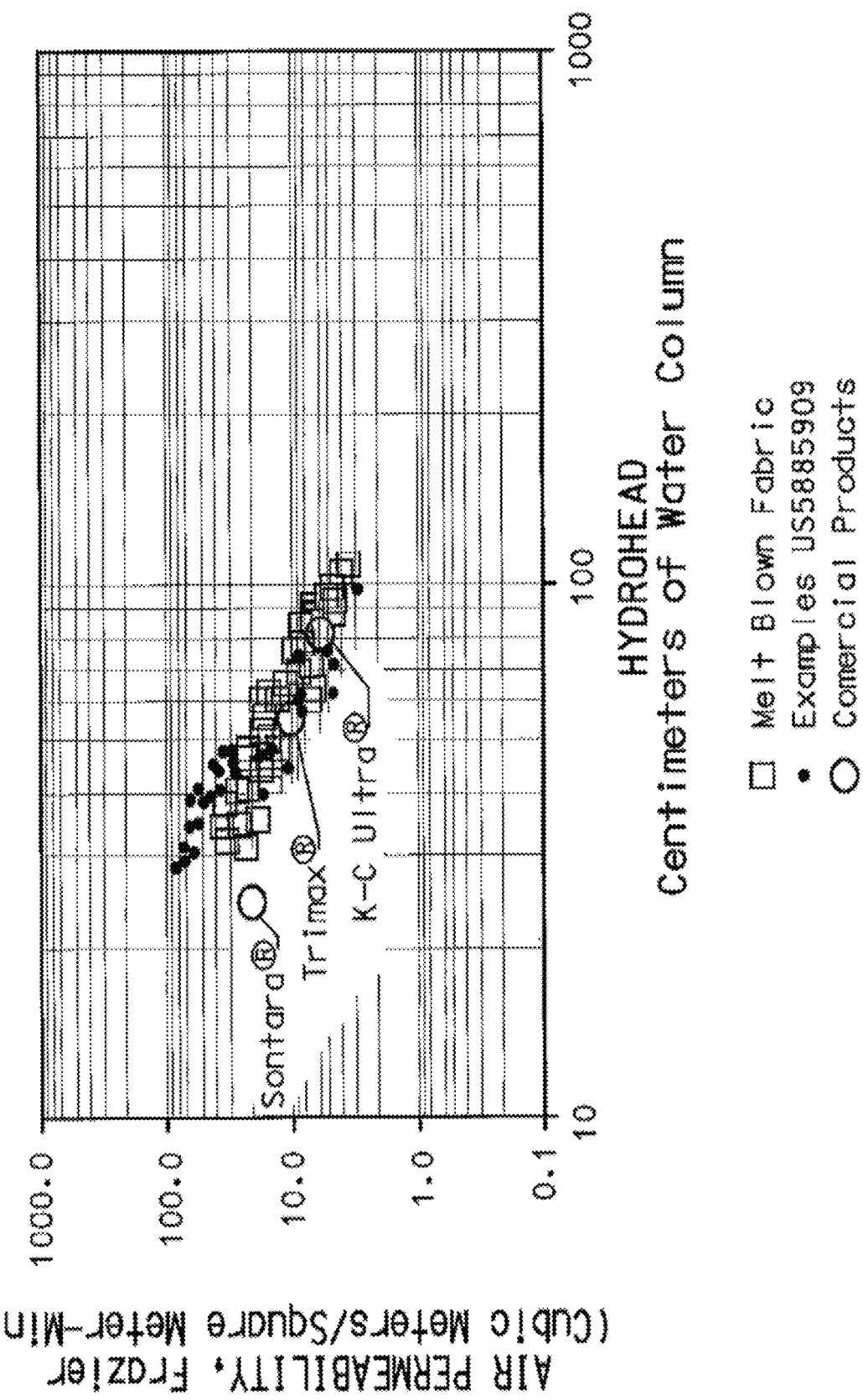
FIG. 3 depicts a graphical representation showing the log-log relationship of liquid hydrostatic head and air permeability of melt blown and commercial nonwoven products.

FIG. 2 depicts a fourth embodiment 100 of the present laminates. Laminate 100 is structurally similar to laminate 10 in that laminate 100 also comprises a cellulosic barrier layer 14 having hydrophobic sizing, and a support layer 18 coupled to the barrier layer. However, laminate 100 differs from laminate 10 in that laminate 100 further comprises an additional spacer layer 34 disposed between barrier layer 14 and support layer 18. As described in more detail below, the spacer layer can comprise a nonwoven, apertured film, or other material that defines a volume that can receive and be occupied by liquid that may undesirably pass through barrier layer 14 to reduce the likelihood of such liquid from also passing through the support layer 18. For example, the free volume in the spacer layer may thereby provide a volume for liquid to occupy on the lower side of barrier layer 14 to reduce the pressure the liquid might otherwise create between barrier layer 14 and support layer 18, and thus reduce the likelihood of that pressure forcing liquid through support layer 18.

In the embodiment shown, spacer layer 34 is bonded to barrier layer 14 via an adhesive 22, and support layer 18 is bonded to spacer layer 34 via an adhesive 22. As described above for laminates 10, 10*a*, and 10*b*, some or all of adhesive layers 22 in laminate 100 can comprise a filamentary adhesive While not shown in FIG. 2, the fiber layer of laminate 100 can include two or more sheets 26 of cellulosic fiber material similar to what is shown and described for barrier layer 14*a* in FIG. 1B. Additionally or alternatively, while not shown in FIG. 2, laminate 100 can also further comprise a stabilization layer 30 similar to what is shown and described for stabilization layer 30 in FIG. 1C.

While suitable for acting as and replacing both a liquid-barrier, such as an inner poly film, and a nonwoven backsheet in disposable absorbent articles, the present laminates—for example 10, 10*a*, 10*b*, 100—can also be used as and replace only the liquid barrier and thus be used with an additional backsheet below our outward of the laminate.

As described in more detail below, embodiments of the present cellulosic barrier layers can be configured to have an air permeability of more than 0.5 ft3/min-ft2 and configured to hold a hydrostatic head of more than 200 mm $H_2O$, for example more than any one of, or between any two of: 200 mm, 300 mm, 400 mm, 600 mm, 800 mm, and/or 1000 mm. Such cellulosic barrier layers may further be incorporated into any of the present laminates 10, 10*a*, 10*b*, 100 in such a way that the overall laminate has air permeability similar to that of the cellulosic barrier layer alone, and/or hydrostatic head that is at least as great as the cellulosic barrier layer alone. For example, a cellulosic barrier layer 14, 14*a* can be coupled to a support layer 18 and/or a stabilization layer 30 that do not substantially reduce the air permeability or the hydrostatic head. Additionally, the present laminates can be configured to remain pinhole free at 400 mm $H_2O$ for 10 minutes. In some embodiments, the present laminates have improved pinhole test performance relative to the cellulosic barrier layer alone. For example, one of the present cellulosic barrier layers 14, 14*a* can be coupled to a support layer 18 of nonwoven material that is selected to improve the pinhole test performance of the combined laminate. In some such embodiments, the nonwoven of the support layer may have a hydrostatic head that is less than or substantially equal to the hydrostatic head of the barrier layer, but still improves the pinhole test performance of the laminate formed when the cellulosic barrier layer and support layer are combined.

A. Cellulosic Fiber Materials as Liquid Barriers

Sheets of cellulosic fiber materials like papers and tissues typically have not been used as liquid barrier materials in disposable absorbent garments due to a variety of factors, such as the tendency of cellulosic fibers to exhibit hydrophilic properties, the tendency of some papers and tissues to exhibit reduced mechanical integrity when wet, and/or the like. Even for those papers and tissues for which mechanical integrity is not significantly reduced by exposure to water, the material may be too porous to act as an effective liquid barrier. In the context of cellulosic fiber materials like papers and tissues, porosity may be thought of in terms of pore size distribution; specifically, a sheet of paper or tissue is defined by a plurality of fibers that define a lattice or collection of fibers that cross and overlap each other to define a plurality of pores within the sheet itself, such that the porosity of the sheet is therefore a function of the sizes and numbers of individual pores, and the distribution of the pores over the area of the sheet. Sheets with consistent fiber size and consistent spatial distribution of fibers will typically have less variation in the size and density of pores than sheets with widely varying fiber sizes or fiber distributions. For example, a sheet with a consistent distribution of relatively small pores may have a low porosity, whereas a sheet with a consistent distribution of relatively larger pores will typically have a higher porosity. As explained in more detail below, an indication of permeability of a sheet of cellulosic fiber sheet may, for example, be determined by measuring air permeability of the sheet. By way of further example, a sheet with a consistent distribution of relatively fewer pores of a given size will have a higher density than a sheet with a consistent distribution of a greater number of pores of the same size. Air permeability is affected by both the number and size of pores in the barrier layer, whereas hydrostatic head is governed primarily by pore size. Pore size distribution can be reduced in papers and tissue by reducing fiber size. An increase in basis weight generally reduces the occurrence of defects, or pinholes, in the cellulosic barrier layer. As explained in more detail below, porosity and pore-size distribution of cellulosic fiber sheets impacts their hydrostatic head, which indicates overall water impermeability, after such sheets are treated with hydrophobic sizing.

A further factor that may complicate the use of papers and tissues as liquid barrier materials is the presence of larger defects, such as pin holes, that are significantly larger than the aggregate pore size for a sheet of material. Various factors can lead to the formation of defects in paper or tissue, such as, for example, the inclusion of larger fibers and/or unintended debris that interrupt the regularity of fiber and pore size distribution in a local area of the paper. Such a defect may be considered a point defect because it is typically localized rather than being a result of typical variations in pore size distribution inherent in the inability to perfectly control the size or distribution of fibers in a slurry from which a sheet of paper or tissue is formed. Point defects can be reduced in papers and tissue by increasing basis weight and/or using higher-quality manufacturing processes to reduce the inadvertent inclusion of larger fibers or debris. As explained in more detail below, the inclusion of local defects in cellulosic fiber sheets impacts their pinhole performance, which indicates water permeability at localized points, even after such sheets are treated with hydrophobic sizing.

As described in more detail below, the present disclosure addresses not only ways to render cellulosic fibers hydrophobic, but also to minimize pore size distribution while preserving air permeability, and to minimize the effects of point defects in cellulosic fiber materials, to render cellulosic fiber materials effective barrier layers for disposable absorbent articles. For example, in at least some applications, it is desirable to maintain an air permeability of greater than 0.5 ft$^3$/min-ft$^2$. One common approach to reducing pore size distribution, reducing variations in pore distribution, and reducing point defects is increasing the basis weight of the paper or tissue. While increasing basis weight does not necessarily minimize the cause of issues impacting liquid barrier performance, it can reduce the impact of those issues. For example, a higher basis weight paper typically also has a greater thickness, which can reduce the likelihood that a point defect or higher concentration of pores will extend through the entire thickness of a sheet and may therefore also reduce the likelihood that such a defect of higher concentration will affect performance of the overall sheet. However, a drawback to this strategy is that increasing basis weight also increases costs. As such, a number of the approaches below seek to reduce basis weight or use sheets of material with basis weights lower than those sheets typically used for similar components in previous disposable absorbent articles.

B. Experimentation and Results

Various prototypes were developed and experiments performed to determine the effects of differences in cellulosic fiber material and basis weight, differences in nonwoven fabric material and basis weight, hydrophobic sizing and application processes, and various other characteristics of the present hydrophobic cellulosic fiber layers, laminates, and disposable absorbent articles. Certain of these variations and their effects of liquid barrier performance are described in more detail below. The present laminates 10, 10a, 10b, 100; hydrophobic cellulosic barrier layers 14, 14a; sheets of cellulosic fiber materials 26; stabilization layers 30; and other components can comprise any of the respective examples described below.

It has been discovered that at least certain uniform, low-porosity cellulosic fiber materials, such as tissues and papers, treated with a hydrophobic finish have a pore size distribution that can provide both high liquid hydrostatic head and high air permeability. Examples of tissue that have been found to be useful in the present invention are Dunn Paper 3207 and Erving 3PT222. It is well known in the paper-making art that cellulosic fibers can be made hydrophobic with alkylketene dimer (AKD), alkenylsuccinic anhydride (ASA), and rosin sizing and other reactive or non-reactive sizing agents that can be applied in the pulp slurry prior to sheet formation or in a finishing step such as a size press or coater to the formed paper sheet. These sizing agents can also be applied after incorporation of the cellulose sheet into the three layer laminate structure. Other examples of finishes for rendering cellulosic tissue hydrophobic are Stantex S6757 manufactured by Pulcra Chemicals, Setilon KNL manufactured by Pulcra Chemicals, Aquesize 404 manufactured by Solv Inc., and fluorochemicals such as Unidyne TG-5243 manufactured by Daiken.

1. Variations in Laminate Layer Basis Weights

A first set of prototypes included three-layer laminates similar in structure to laminate 10b shown in FIG. 1C. Before the tissue was treated with an aqueous solution of AKD, an adhesively-bonded, three-layer laminate was made with a middle layer of tissue and outer layers of spunbond or SMS nonwoven made of polypropylene fibers. Adhesively-bonded spunbond or SMS nonwoven layers were unaffected by water and stabilized the tissue during wetting and drying with the AKD solution. The support and stabilization layers also reduce the strain imparted to the tissue layer during converting and use of absorbent products containing the laminate. A high extensibility of the tissue, imparted by its creped structure, is believed to an important factor in reducing pinhole formation in stretched and folded laminates. Another important attribute of creped tissue for the present cellulosic barrier layers is that it has more of a cloth-like, rather than a paper-like, feel and sound when it is handled. Basis weight of the synthetic fiber nonwovens was in the range of 8-42 gsm and basis weight of the tissue was in the range of 17-36 gsm. Typical adhesive add-on was in the range of 3-6 gsm, although it is believed that lower levels of adhesive may be possible. Savare CB710 and E60W adhesives were found to be effective for stabilizing the tissue in the laminate during the finishing step. In other embodiments, non-adhesive methods of lamination such as thermal or ultrasonic bonding may be used instead of or in addition to adhesive.

After the laminates were made, they were treated in an aqueous solution of AKD at room temperature and dried. Fennosize KD 266 MB supplied by Kemira, with an active concentration of 15.5%, was used to treat the laminates. Target add-on of AKD solids was 0.01 g. AKD solids per g. of laminate. This value was calculated for a wet pick-up of 4 g. of solution per g. of laminate for a solution containing 3.1 g. of AKD per 1000 g. of solution in a 50× dilution of Fennosize KD 266 MB. As shown in TABLE 1 below, a 50× dilution was defined as 20 g. of Fennosize KD 266 MB, at 15.5% solids, diluted with 980 g. of water. The laminate for which data is shown in TABLE 1 was not calendared after being saturated with the solution. When other laminates were calendared after being saturated with the solution, the wet pick of solution on the laminate was reduced to a range of about 1 g. solution per g. of laminate, and the dilution of AKD was reduced to maintain a target add-on of 0.01 g. AKD solids per g. of laminate. Hand-treated samples were dried and cured on a bench-scale Emerson Speed Dryer for 4-10 min. at a surface temperature of 110°-125° C.

TABLE 1

Example showing 50X dilution of Fennosize KD 266 MB solution (i.e. 1000 g./20 g. = 50X)

| Component | Wt. (g) | Wt. Fraction | Wt. (g) |
| --- | --- | --- | --- |
| AKD Solids | 20 | 0.155 | 3.1 |
| Solution Water | 20 | 0.845 | 16.9 |
| Make-up Deionized Water | 980 | 1.000 | 980 |
| Total | — | — | 1000 |

Figure 4:
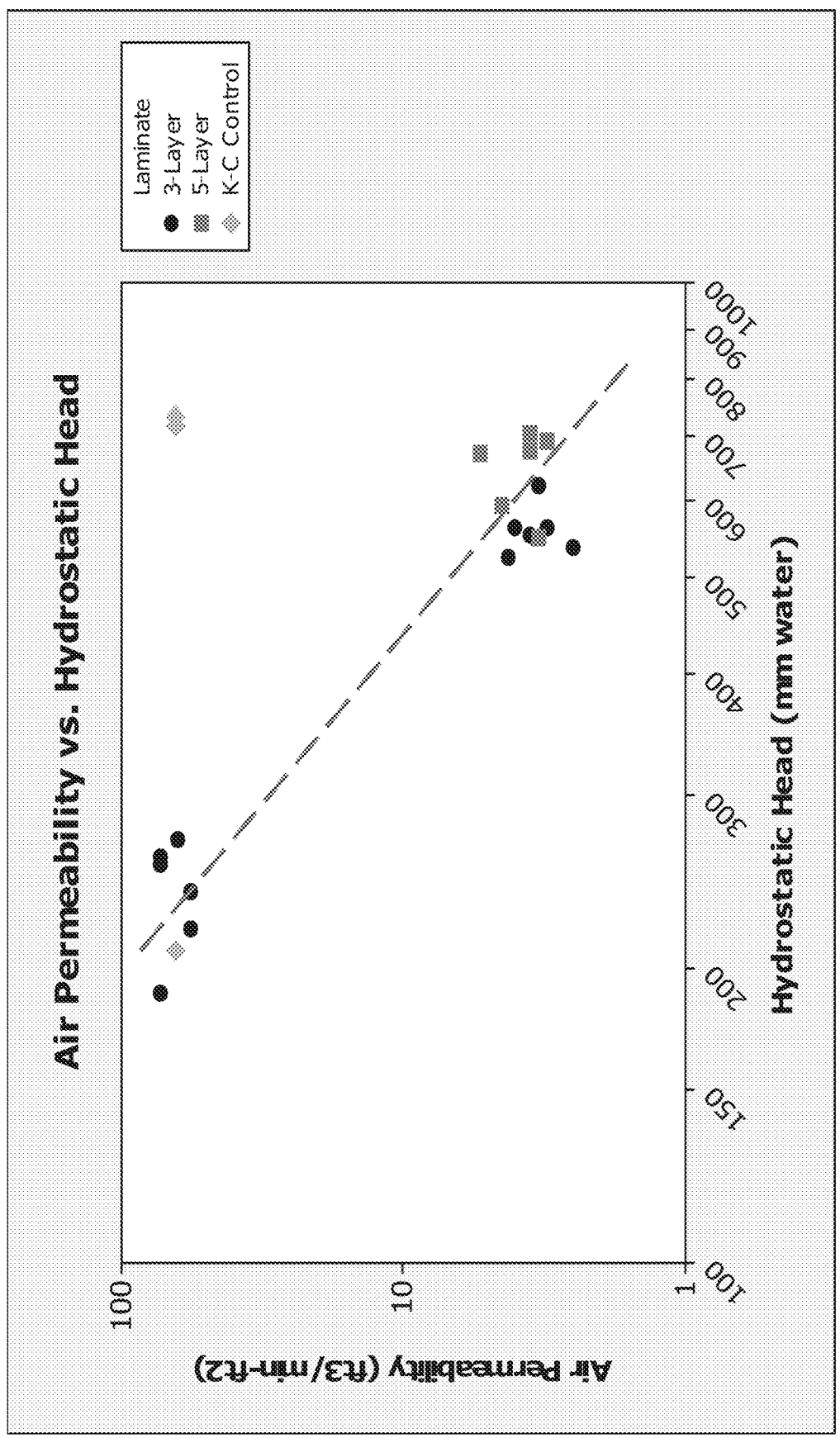
FIG. 4 depicts a graphical representation showing the relationship of liquid hydrostatic head and air permeability of nonwoven materials and the an embodiment of the present laminates.

FIG. 4 shows the relationship between air permeability and liquid hydrostatic head for laminates made with 17 gsm and 36 gsm tissue. For purposes of this disclosure, air permeability is measured as Frazier air permeability using ASTM D737-04, "Standard Method for Air Permeability of Textile Fabrics," as described in Section H entitled "Air Permeability." This test method is used to determine the rate of air flow passing perpendicularly through a known area under a prescribed air pressure differential between the two surfaces of planar material. For purposes of this disclosure, hydrostatic head—which may also be referred to as "hydrohead" or "HH"—is measured using AATCC Test Method 127-2008, "Water Resistance: Hydrostatic Pressure Test," as described in Section I entitled "Hydrostatic Head Test." This test method is used to measure the resistance of a sheet of material to the penetration of water under hydrostatic pressure. Higher values of hydrostatic head were achieved for laminates made with the higher basis weight tissue but air permeability was decreased. For these prototypes, basis weight of the outer layers of synthetic nonwoven had no measurable effect on the air permeability of the laminates. K-C Control in FIG. 4 was an SMS nonwoven from a surgical gown. It had high air permeability but high variability in hydrostatic head performance. Also in FIG. 4, results for a 5-Layer laminate including the above-described 3-layer laminate with one additional 17 gsm tissue and one additional 10 gsm synthetic nonwoven layer showed that the additional layers had little effect on air permeability and hydrostatic head. Overall, air permeability and hydrostatic head were driven by the basis weight of the tissue in the laminate. As noted below, tissue formation quality and level of crepe are also factors that can affect air permeability and hydrostatic head. Hydrostatic head increased with increasing add-on of AKD down to a dilution of about 100×-50× for 4 g/g wet pick-up, and did not increase at lower levels of dilution corresponding to higher levels of AKD add-on. AKD add-on level had little effect on the air permeability of the laminate.

Pinhole testing of the backsheet laminate provided an additional measure of the liquid barrier performance of the laminate. A pinhole is a spot on the laminate where liquid breakthrough had occurred at an applied pressure of 400 mm, 600 mm, or 800 mm water after a given period of time, usually 10 minutes. Generally, a backsheet material will be required to be free of pinholes when subjected to a static pressure of greater than about 600 mm of water for at least 10 minutes. The Pinhole Test Method used for these prototypes is described below in Section E entitled "Pinhole Test Method," which test method, for purposes of this disclosure, defines how to determine whether a material remains pinhole free at a given pressure when a Modified Pinhole Test Method or a Liquid-Column Pinhole Test Method are not specified. TABLE 2 summarizes results of testing of various materials using this Pinhole Test Method. A woven polyester/cotton fabric, referred to as PET/Cot in TABLE 2, provided high air permeability but absorbed water and had no measureable hydrostatic head. MicroP, one of the so-called "breathable" microporous poly films that is commercially available exhibited a high hydrostatic head, up to its tearing strength, and is known to be somewhat permeable to the diffusion of water vapor, but it had no meaningful air permeability. These microporous films provide good pinhole performance because they do not have defects or pinholes unless they are damaged in converting. An SMS nonwoven used in a commercially available KC200 surgical gown had high air permeability and good, although highly variable, hydrostatic head. Pinholes were generated with this material at a pressure of 600 mm water indicating that this material would probably not make an acceptable backsheet for an absorbent product. The Attends, Medline, and Tena materials in TABLE 2 were synthetic nonwoven backsheet nonwovens from special types of commercially-available air-permeable bed pads. The nonwovens had high air permeability but the bedpads from which they were obtained are known to pass liquid through the backsheet, consistent with the poor pinhole test performance shown here.

The 4a laminate in TABLE 2 was an adhesively-bonded, three-layer laminate comprised of two layers of spunbond nonwoven and a central layer of 36 gsm tissue. The laminate was treated using an AKD solution at 50× dilution to provide an add-on of 0.01 g. of AKD solids per g. of laminate. The laminate had a hydrostatic head over 500 mm water and a measurable air permeability. There were no pinholes observed for this laminate, even at an applied static pressure of 800 mm water. Testing revealed that the hydrostatic head test could only provide an estimate of pinhole performance at a given pressure. This may be due to the fact that pressure in the pinhole test used for these prototypes can be relieved when liquid is expressed from the edges of the laminate being tested. The prototype 4a laminate may function well as a backsheet with a somewhat low, but acceptable, level of air permeability. Laminate 1a was made in the same way as 4a except that it was made using a tissue of only 17 gsm basis weight. It had high air permeability but lower values of hydrostatic head. Pinholes were observed at an applied pressure of only 400 mm water. Due to the pinhole results at 400 mm, pinhole tests were not performed at higher pressures. This 1a laminate would probably not make a good backsheet material in disposable absorbent articles subject to higher pressures.

As indicated for prototype laminate 2a in TABLE 2, an unexpected discovery was made when the 10 gsm spunbond of the support layer like layer 18 in FIG. 1C on the non-liquid-contacting outer or lower side of the laminate was replaced with a 17 gsm SMS nonwoven. Pinhole performance improved dramatically. The 17 gsm nonwoven material is known to have a hydrostatic head in the range of only about 120-150 mm water, but it was capable of enhancing the pinhole performance of the laminate such that the laminate was free of pinholes at a pressure of 800 mm water. This 2a laminate with a high air permeability of 59 ft$^3$/min-ft$^2$ would make a very good backsheet material for a wide variety of disposable absorbent garments, including those subjected to higher pressures during use. Because of the affinity of cellulose fibers for water, there may be some reduction in pinhole performance of these laminates when pinhole performance is assessed at longer times.

TABLE 2

Hydrostatic head (HH), air permeability, and Pinhole Test Method performance at various static pressures for prototypes 4a, 1a, 2a, and reference materials

| Material | Layers (nw/tissue/nw) | AKD Dilution | HH (mm H$_2$O) | Air Permeability (ft$^3$/min-ft$^2$) | Pinhole Test Method results (# of pinholes) | | |
|---|---|---|---|---|---|---|---|
| | | | | | 400 mm H$_2$O | 600 mm H$_2$O | 800 mm H$_2$O |
| PET/Cot | 120 gsm | | 0 | 33 | High | High | High |
| MicroP | | | >>150 | 0.03 | 0 | 0 | 0 |
| KC200 | 35 gsm | | 209-734 | 65 | 0 | 2 | 7 |
| Attends | 40 gsm | | 12-17 | 250 | 25 | 17 | 30 |
| Medline | 35 gsm | | 10-12 | 459 | 33 | 24 | 27 |
| Tena | 42 gsm | | 16-19 | 323 | 7 | 20 | 20 |
| Prototype 4a | 10/36/10 gsm | 50X | 525-566 | 4 | 0 | 0 | 0 |
| Prototype 1a | 10/17/10 gsm | 50X | 189-255 | 73 | 20 | — | — |
| Prototype 2a | 10/17/17 gsm | 50X | 219-270 | 5 | 0 | 0 | 0 |

2. Variations in Hydrophobic Sizing

Treatment of the three-layer laminate structure similar to laminate 10b shown in FIG. 1C to make the cellulosic layer hydrophobic using a variety of chemistries was also investigated. A laminate consisting of a 10 gsm spunbond stabilization layer similar to layer 30 in FIG. 1C, a 17 gsm tissue cellulosic barrier layer similar to layer 14 in FIG. 1C, and a 42 gsm spunbond support layer similar to layer 18 in FIG. 1C was hand treated in the lab with solutions of different chemistries. All treatment was done at a solution concentration of 0.31% solids. Chemicals tested included AKD in the form of Fennosize KD266 MB from Kemira, Aquesize 404 from SOLV, Inc., Stantex S6767 form Pulcra Chemical, Unidyne TG-5243 from DAIKEN America, Inc., and a longer chain AKD in the form of Eka DR 28 HF from Kemira. Target add-on was 0.01 gram (g) of solids per gram of laminate. Hand-treated samples were dried and cured on a bench-scale Emerson Speed Dryer for 4-10 min. at a surface temperature of 110°-125° C. TABLE 3 summarizes the results of testing for hydrohead on the treated samples compared to a laminate with no chemical treatment. As shown in Table 3, even tissue layers with basis weights as low as 17 gsm can be treated to have a hydrohead approaching or even exceeding 200 mm H2O. Tissues and papers with higher basis weights will often have higher hydrohead values when subjected to similar treatments.

TABLE 3

Hydrostatic head of 10/17/42 (10 gsm spunbond nonwoven/17 gsm tissue/42 gsm spunbond nonwoven) laminate treated with various chemistries

| Chemical Treatment | Hydrohead (mm water) |
|---|---|
| Untreated | 113 |
| Fennosize KD 266 MB | 194 |
| Aquesize 404 | 126 |
| Stantex S 6767 | 160 |
| Unidyne TG-5243 | 204 |
| Eka DR 28 HF | 140 |

3. Variations in Cellulosic Fiber Sheet Properties

Key properties of the cellulosic fiber sheet of the present cellulosic barrier layers, and their impact on hydrohead was also investigated. Key properties identified for investigation were basis weight, percent elongation, degree of wet strength as measured by the ratio of wet/dry MD tensile, and air permeability. As discussed throughout this disclosure, basis weight and porosity impact hydrohead. Between percent elongation and wet tensile, only percent elongation was indicated to be significant. Percent elongation was believed to be significant due to the ability of a cellulosic barrier layer with high elongation to accommodate in-plain strain during stretching or folding without developing pinhole defects. Commercially produced dry-creped tissue papers from Dunn tissue—specifically, grades 3207, 3495, 6327, 3423, 3335, 3429, 6407 and 3283—were used to produce laminate structures with 10 gsm spunbond upper layer and 42 gsm spunbond backsheet. The laminates were hand treated in a laboratory with a solution of 0.31% solids at 50x dilution AKD in the form of Fennosize KD266 MB from Kemira.

The laminates were dried and cured on a bench-scale Emerson Speed Dryer for 4-10 min. at a surface temperature of 110°-125° C. In the hydrohead test, the sample laminate is secured to the bottom of a cylinder that is filled with water at a steady rate. During the test, the pressure of the water causes the laminate samples to bulge out of the horizontal plane. At the extreme, the stress caused by this bulging at the edges of the cylinder can cause the sample to tear. This is especially true for lightweight materials such as the tissue paper grades being tested. To evaluate the impact of the sample bulging out of plane on the hydrostatic head value, tests were conducted with a mesh screen placed under the test sample to support the sample and prevent the out of plane bulging. Table 4 shows results of the hydrostatic head in normal hydrohead testing in which the sample is unsupported, and in a modified hydrohead with the sample supported, for the various tissue grades studied. Percent elongation or % elongation, for purposes of this disclosure, is measured using the TAPPI/ANSI Standard T-494 om-13 entitled "Tensile properties of paper and paperboard (using constant rate of elongation apparatus)," as described in Section J entitled "Percent Elongation Test Method." Samples with a low degree of crepe as measured by a percent elongation of 12% or less, show an increase in hydrohead when the sample is supported compared to when unsupported. This suggest a degree of crepe sufficient to give a higher percent elongation can be beneficial in preventing loss of water resistance if the laminate is stretched when the absorbent article is in use.

TABLE 4

Hydrostatic head of laminates made with 10 gsm spunbond upper layer and 42 gsm spunbond backsheet with various grades of tissue

| Grade ID | BW (gsm) | Percent Elongation (%), MD | Hydrohead, supported (mm water) | Hydrohead, unsupported (mm water) | Difference (mm water) |
|---|---|---|---|---|---|
| 3495 | 20.3 | 7 | 205 | 188 | 17 |
| 6327 | 18.7 | 9 | 200 | 177 | 23 |
| 2423 | 20.3 | 9 | 192 | 160 | 32 |
| 3335 | 21.2 | 12 | 190 | 152 | 38 |
| 3429 | 24.4 | 12.5 | 202 | 202 | 0 |
| 6407 | 16.3 | 19 | 177 | 177 | 0 |
| 3283 | 17.9 | 21 | 165 | 173 | −8 |

4. Two-Layer Laminate Prototypes

Because of the process complexity of forming a three-layer laminate and chemically treating the laminate to make the cellulose layer hydrophobic, addition of sizing chemistry during formation of the cellulose fiber sheet was investigated. Cellulose sheets were prepared on a commercial Fourdrinier paper machine using different combinations of fiber furnish to create a pore structure required to provide both high hydrohead and high air permeability. Bleached northern softwood kraft was used as the primary furnish component to provide a relatively open structure to the fiber sheet. The addition of caustic treated softwood fiber, specifically HPZ (L1) from GP cellulose, was used to increase the bulk of the fiber sheet and further open the structure for increased air permeability. Eucalyptus fiber was used as a source of small, uniform fibers that could fill in the open spaces in the sheet structure to reduce pore size and help to reduce pinhole-type failures but still have enough small pores to provide air permeability. Sizing chemical, Fennosize KD266 MB AKD from Kemira, was added to the fiber slurry prior to sheet formation. Addition rate was varied from 2-10 dry lb/ton. It was found that at addition rates above 8 dry lb/ton or 0.004 g/g, the water contact angle of the paper was above 90 degrees, indicating the fiber sheet was hydrophobic. Wet strength chemical, Fennostrength 4063 from Kemira, was added to the fiber slurry prior to sheet formation at 2 dry lb/ton. The paper was made at basis weight of 32.5 gsm. It was discovered that variations in the furnish composition produced changes in both air permeability and hydrohead, even with the same level of chemical treatment.

Table 5 shows the results for paper sheets made with five different mixtures of the different fiber types. All of these papers were produced using 8 lb/ton of AKD and have contact angles greater than 90 degrees. The degree of sizing was also measured using the Hercules Sizing Test defined by TAPPI/ANSI Standard T-530 om-12 using 65% reflectance, which standard is incorporated by reference in its entirety. Test samples were aged in a 100 C oven for 5 minutes prior to testing. HST values are generally greater than 1000 seconds, indicating a high degree of sizing. Use of increasing amounts of HPZ fiber had the anticipated impact of increasing the air permeability with an accompanying loss in hydrostatic head. Also as expected, increasing the amount of eucalyptus fiber at a similar level of HPZ fiber usage increased the hydrostatic head, but decreased the air permeability. These results are in line with the conceptual model of creating an open lattice structure with northern softwood and HPZ (L1) from GP Cellulose, with the eucalyptus fiber filling in the larger spaces within the lattice structure.

TABLE 5

Sizing levels, hydrohead, and air permeability of papers made with different combinations of northern softwood kraft, HPZ and eucalyptus fiber with the addition of AKD to the fiber slurry prior to sheet formation

| Paper Furnish | AKD added to furnish (lb/ton) | Hercules Size Test (sec), 65% Reflectance, Aged | Contact Angle (degrees), wire/felt | Hydrostatic Head (mm water) | Frazier air permeability (ft$^3$/min-ft$^2$) |
|---|---|---|---|---|---|
| 12% Eucalyptus/88% Northern Softwood | 8 | 1221 | 118/114 | 428 | 1.2 |
| 12% Eucalyptus/4% HPZ/ 84% Northern Softwood | 8 | 1557 | 115/118 | 372 | 1.8 |
| 14% Eucalyptus/9% HPZ/ 78% Northern Softwood | 8 | 1131 | 100/102 | 309 | 2.3 |

TABLE 5-continued

Sizing levels, hydrohead, and air permeability of papers made with different combinations of northern softwood kraft, HPZ and eucalyptus fiber with the addition of AKD to the fiber slurry prior to sheet formation

| Paper Furnish | AKD added to furnish (lb/ton) | Hercules Size Test (sec), 65% Reflectance, Aged | Contact Angle (degrees), wire/felt | Hydrostatic Head (mm water) | Frazier air permeability (ft 3/min-ft 2) |
|---|---|---|---|---|---|
| 30% Eucalyptus/20% HPZ/ 50% Northern Softwood | 8 | 1616 | 101/93 | 313 | 3.3 |
| 18% Eucalyptus/18% HPZ/ 64% Northern Softwood | 8 | 1173 | 104/93 | 237 | 4.5 |

Table 6 summarizes the results of pinhole testing on the papers made with various furnish conditions, which pinhole testing was completed using the Liquid-Column Pinhole (Soft-Hard) Test Method defined in Section F entitled "Liquid-Column Pinhole Test Method," and which test method applies the pressure with a column of water rather than a weight. Nine replicates were tested for each condition to provide a more complete picture of pinhole performance. In general, pinholes can occur because the pore size or contact angle of the material is insufficient to prevent water penetration, or it can occur because of a localized defect in the material that is unrelated to the general pore size distribution in the material. Testing of multiple replicates increases the potential of identifying localized defects in the paper samples. All of the papers showed very good pinhole performance with at least 8 of 9 samples having zero pinholes up at 800 mm water. The two papers that had one of the samples fail with pinholes did so at low pressure of 400 mm water, indicating this was likely a localized defect in the paper and not reflective of the overall paper structure. Surprisingly, the materials were free of pinholes at higher pressure than may have been expected based on the hydrohead values. It is believed that some of the moisture from the saturated paper towel used in the test to simulate a wet absorbent core diffuses into the paper in the form of water vapor and is absorbed by the cellulose fiber causing swelling over the time of the test, thereby reducing the effective pore size of the material. This may represent a potential advantage to a cellulose layer over a synthetic material.

TABLE 6

Pinhole test results for papers made with different combinations of northern softwood kraft, HPZ and eucalyptus fiber

| | Percent of samples with no pinholes using Liquid-Column Pinhole (Soft-Hard) Test Method | | |
|---|---|---|---|
| Paper Furnish | 400 mm water | 600 mm water | 800 mm water |
| 12% Eucalyptus/88% Northern Softwood | 100 | 100 | 100 |
| 12% Eucalyptus/4% HPZ/ 84% Northern Softwood | 100 | 100 | 100 |
| 14% Eucalyptus/9% HPZ/ 78% Northern Softwood | 88.9 | 88.9 | 88.9 |
| 30% Eucalyptus/20% HPZ/ 50% Northern Softwood | 100 | 100 | 100 |
| 18% Eucalyptus/18% HPZ/ 64% Northern Softwood | 88.9 | 88.9 | 88.9 |

The prototype papers in Table 5 and Table 6 were produced on a conventional Fourdrinier paper machine with no on-machine dry creping. As noted earlier, one of the potential advantages of using tissue as the cellulose sheet is the crepe imparted in commercial tissue, providing a degree of extensibility that has potential to prevent pinhole formation in folded or stretched absorbent products and to have a more cloth-like feel. The papers produced with no on-machine creping were noticeably stiffer with less drape and more noisy when handled than the commercial tissue papers used in producing the three-layer laminates. To overcome these limitations, the paper made with 30% Eucalyptus/20% HPZ/ 50% Northern Softwood was dry creped in an off-machine process at Micrex in Walpole, Mass. to two levels of creping, 49% elongation and 53% elongation. The paper after creping had significantly more drape and was much less noisy during handling than the uncreped paper. The dry crepe process resulted in an increase in sheet basis weight from 32.5 gsm to 42 gsm and 44 gsm for the two levels of crepe. It was anticipated that dry creping of the paper would enhance the air permeability of the paper but potentially reduce the hydrostatic head and/or pinhole performance.

Table 7 summarizes the Frazier air permeability, hydrohead and pinhole performance of the creped and uncreped papers. For the pinhole testing, nine replicates were tested as have been previously using the Liquid-Column Pinhole (Soft-Hard) Test Method defined in Section F entitled "Liquid-Column Pinhole Test Method." As expected, creping the paper significantly increased the air permeability. Unexpectedly, the creped paper had higher hydrohead levels than the uncreped paper. In addition, the creped paper had pinhole performance comparable to the uncreped paper at a level of 1000 mm water. The results indicate that the creping process does not significantly damage the paper structure in a manner that would reduce its potential to prevent water penetration. It is speculated that the increase in basis weight and bulk with creping may produce a more tortuous pathway for water to traverse through the paper sheet, resulting in an increase in the hydrostatic head.

TABLE 7

Impact of off-line dry creping of paper made with 30% Euc/20% HPZ/50% SW on air permeability, hydrostatic head and pinhole performance

| Paper Treatment | Frazier air permeability (ft 3/min-ft 2) | Hydrohead (mm water) | Percent of samples with no pinholes at 1000 mm water using Liquid-Column Pinhole (Soft-Hard) Test Method |
|---|---|---|---|
| Uncreped paper | 3.3 | 313 | 88.9 |
| Creped paper (49% elongation) | 9.8 | 430 | 88.9 |
| Creped paper (53% elongation) | 10.5 | 385 | 77.8 |

Another potential explanation for the increase in hydrohead may be due to the extensibility of the creped paper. In the hydrohead test, the sample is secured to the bottom of a cylinder that is filled with water at a steady rate. During the test, the pressure of the water causes the paper samples to bulge out of the horizontal plane. At the extreme, the stress caused by this bulging at the edges of the cylinder can cause the sample to tear. This is especially true for lightweight materials such as the paper being tested. To help prevent tearing of the paper, the samples are sandwiched between two layers of 42 gsm nonwoven, each layer having a very low hydrohead of less than 100 mm water, but even with the support of the nonwoven the samples will still bulge out of plane. As described above in connection with Table 4, additional materials were subjected to hydrostatic head testing using the normal test protocol in which the sample is unsupported, and using a supported test protocol with a mesh screen placed under the test sample to support the sample and prevent the out of plane bulging. Table 8 shows results of the unsupported and supported hydrostatic head tests for both the uncreped paper and paper creped to 49% elongation. For the uncreped paper, the hydrohead value when the sample is supported is statistically significantly different, $P<0.05$, than the regular hydrohead value in which the sample is unsupported. For the creped paper there is no statistically significant difference. The higher elongation of the crepe paper may allow it to bulge under the pressure of the hydro head test without developing open area to allow water to pass through. This would result in a higher water level, measured in mm of water, before 3 drops of water emerge through the non-wetted side of the sample which is the stopping point for the hydrohead test. The potential to resist some level of stretching without allowing water to pass could translate to increased effectiveness in preventing leakage of the creped material in an absorbent product subject to stretching during use.

TABLE 8

Difference in hydrostatic head test value with and without sample support for creped and uncreped paper

| Paper Treatment | Hydrohead Supported (mm water) | Hydrohead Unsupported (mm water) | Difference (mm water) | t-test on difference, p-value |
|---|---|---|---|---|
| Uncreped paper | 381 | 313 | 67.8 | 0.037 |
| Creped paper (49% elongation) | 437 | 430 | 7 | 0.854 |

C. Disposable Absorbent Articles

Figure 6A:
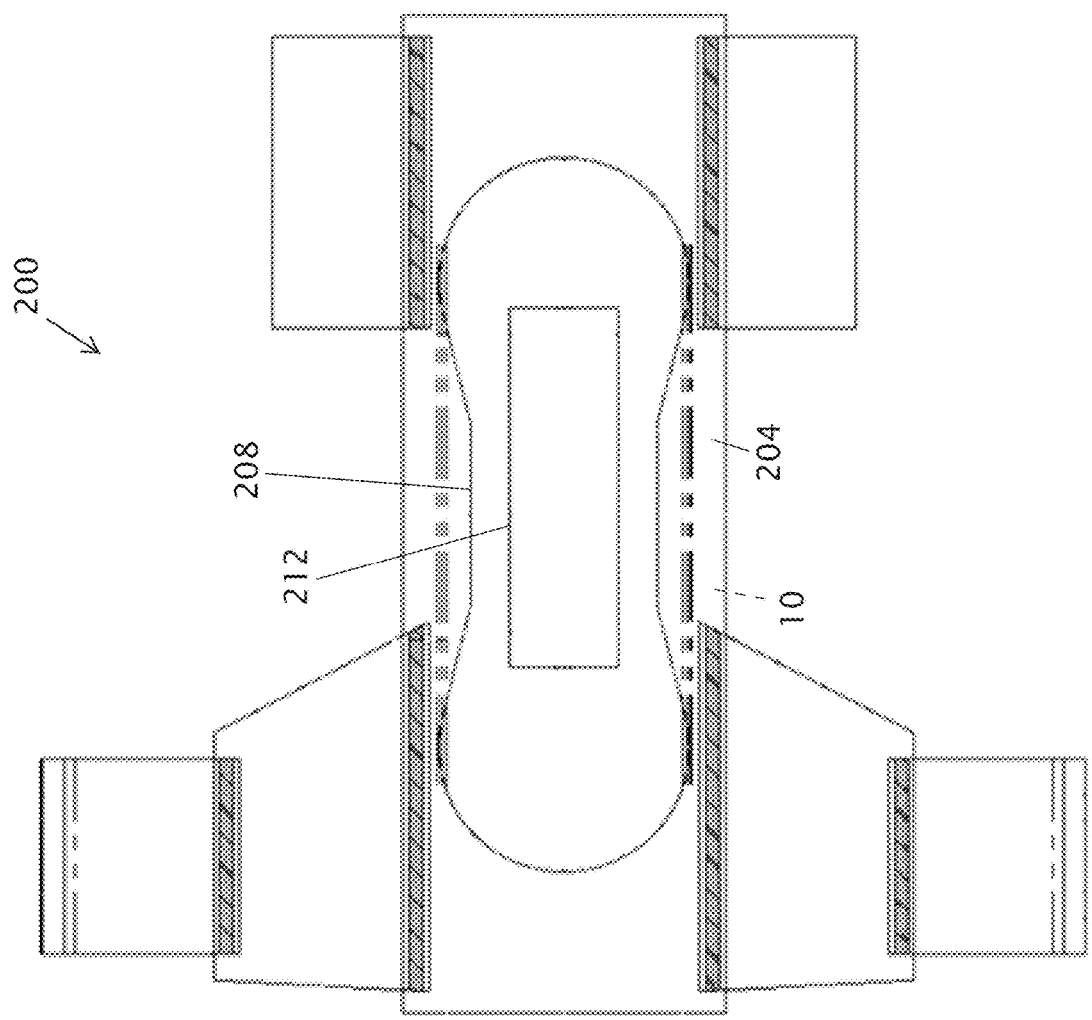
FIGS. 6A and 6B depict top and cross-sectional views, respectively of one embodiment of the present disposable absorbent articles.
Figure 6B:
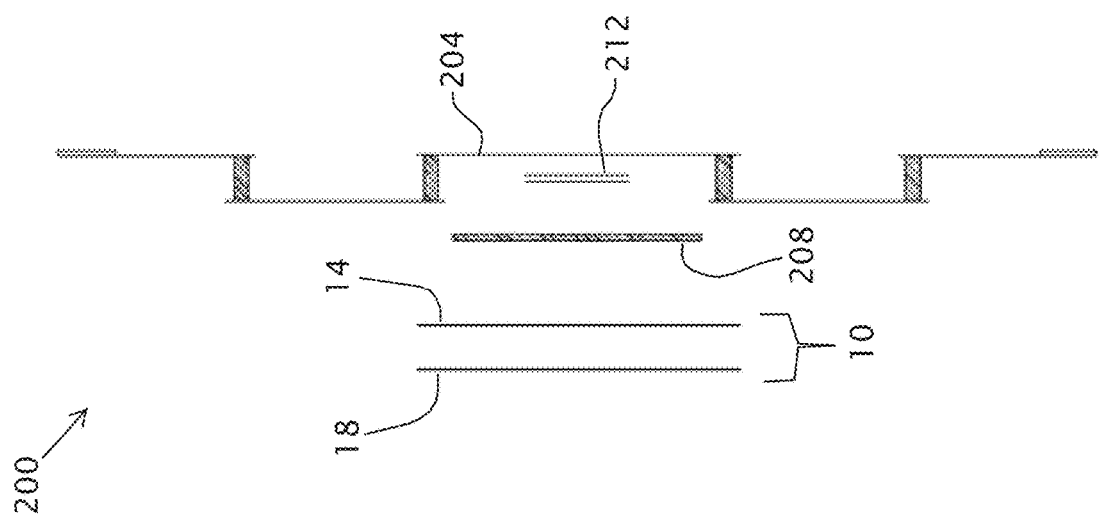

As noted above, the present cellulosic fiber layers can include hydrophobic sizing and be configured to function as breathable barrier layers in disposable absorbent articles. One embodiment 200 of the present absorbent articles is shown in FIGS. 6A and 6b. In this embodiment, article 200 is an adult brief. In this embodiment, article 200 comprises one of the present laminates 10 that is configured to function as a breathable backsheet assembly, a liquid permeable topsheet 204, and an absorbent core 208 positioned between topsheet 204 and laminate 10. In this embodiment, absorbent core 208 comprises cellulosic fibrous material and/or superabsorbent polymeric (SAP) particles. In the embodiment shown, article 200 also includes an optional acquisition-distribution layer (ADL) 212.

As shown, laminate 10 is coupled to topsheet 204 such that barrier layer 14 is above and inward of supporting layer 18, and supporting layer 18 forms the lowermost or outermost surface of the corresponding portion of article 200. For example, laminate 10 may bonded to topsheet 204 via an adhesive, ultrasonic bonds, and/or any other bonding method or structure that is sufficiently durable to permit the article to function as intended during use. In other embodiments, and as described above with reference to FIG. 2, article 200 may further include an additional backsheet layer like layer 34 below supporting layer 18 such that the additional backsheet layer forms the outermost layer of the article.

Other examples of disposable absorbent articles in which the present cellulosic barrier layers and laminates be used as liquid barrier layers and/or backsheets include, infant diapers, adult pull-up underwear, and bladder control pads, bed pads, feminine hygiene products, and surgical gowns, drapes, and masks. Some embodiments of the present laminates are configured with particular properties for particular types of disposable absorbent articles. For example, some types of disposable absorbent articles may perform better with different combinations of minimum values of air permeability, hydrostatic head, and pinhole performance, as indicated in Table 9 below. Of the minimum values indicated in Table 9, the cellulosic barrier layer may itself have the minimum values of permeability and hydrostatic head, and/or the combined laminate may have the minimum values of permeability and hydrostatic head. Conversely, the minimum pinhole performance listed in Table 9 is more typically of the combined laminate including at least a cellulosic barrier layer and a nonwoven support layer, and sometimes including one or more additional layers or components, such as, for example, a stabilization layer like layer 30 of FIG. 1C, a compressible layer like layer 216 of FIG. 7A, and/or the like. The pinhole values for Table 9 correspond to values to be obtained with the Liquid-Column Pinhole (Soft-Hard) Test Method defined in Section F entitled "Liquid-Column Pinhole Test Method." While Table 9 specifies values to be obtained with the Liquid-Column Pinhole (Soft-Hard) Test Method for some embodiments of the listed absorbent articles, other embodiments of the listed absorbent articles can have the specified pinhole-free performance values under any one of the other pinhole test methods described in this disclosure.

TABLE 9

Laminate configurations for absorbent articles types

| Absorbent Articles | Air Permeability (ft³/min-ft²) | Hydrostatic Head (mm H₂O) | Pinhole Free Performance using Liquid-Column Pinhole (Soft-Hard) Test Method |
|---|---|---|---|
| Bladder Control Pad | 1.5 | 400 | 600 mm H₂O for 10 minutes |
| Adult Brief | 0.5 | 600 | 800 mm H₂O for 10 minutes |
| Adult Pull-Up Underwear | 1.5 | 400 | 600 mm H₂O for 10 minutes |
| Baby Diaper | 0.5 | 600 | 800 mm H₂O for 10 minutes |
| Regular Bedpad | 1.5 | 400 | 600 mm H₂O for 10 minutes |
| Air-flow Bedpad | 20 | 200 | 400 mm H₂O for 10 minutes |

D. Further Variations on the Present Hydrophobic Cellulosic Fiber Layers, Laminates, and Disposable Absorbent Articles A relatively high value of hydrohead must be maintained in a breathable backsheet in order to provide sufficient liquid barrier properties for good performance in an absorbent product. Higher values of hydrohead for a breathable backsheet laminate will generally improve its pinhole performance, but these values do not necessarily correlate in a simple way. Attempts to understand factors that can affect the correlation between hydrohead and pinhole performance have led to additional variations for improving the liquid barrier properties of laminates and absorbent articles that include the present cellulosic barrier layers.

1. Additional Compressible Layer

In some of the present embodiments, a relatively soft or compressible layer is disposed on either the inside or outside of the present cellulosic barrier layers, for example, immediately above and/or immediately below one of the present cellulosic barrier layers. To illustrate the way in which such an additional compressible layer can impact the liquid barrier performance of the present cellulosic barrier layers, FIG. 5 shows how pinhole performance changed for some absorbent products, specifically prototype bedpads, as a function of hydrohead of the breathable backsheet and the compliance of the surfaces supporting and applying pressure to the products. To generate the data shown in FIG. 5, a Modified Pinhole Test Method was used in which: (a) pressure was applied by a soft rubber surface while the sample was supported by a soft rubber surface ("soft/soft"); (b) pressure was applied by a soft rubber surface while the sample was supported by a hard rubber surface ("soft/hard"); and (c) pressure was applied by a hard rubber surface while the sample was supported by a hard rubber surface ("hard/hard"). This Modified Pinhole Test Method is described in Section G entitled "Modified Pinhole Test Method" which test method, for purposes of this disclosure, describes the method for determining whether a material remains pinhole free under a given pressure or column of water using the Modified Pinhole (Soft-Soft) Test Method, the Modified Pinhole (Soft-Hard) Test Method, or the Modified Pinhole (Hard-Hard) Test Method.

Prototype bedpads in FIG. 5 were made with different breathable backsheets. All of the products contained the same airlaid absorbent core. A "0" in the figure indicated that there were "no pinhole leaks" in a pinhole test at a given pressure for 10 minutes. A "4P", for example, indicated that there were four pinholes and "CS" indicated complete saturation of tissue placed on the outside of the backsheet to identify a leak. Pinhole performance improved, as expected, with increasing hydrohead of the backsheet laminate. Surprisingly, pinhole performance was also affected by the compliance of the surfaces used in the test to apply the pressure. Pinhole performance was best when the pressure was applied between two soft surfaces of sponge rubber and worst when the pressure was applied between two hard rubber surfaces. Within each of these groups, pinhole performance generally decreased with increasing hydrostatic head over the range of 400 to 800 mm H₂O. These observations may be a result of stress concentrations which were amplified by the harder surfaces in nonuniform areas of the backsheet. It was surprising to learn that the pinhole performance of an absorbent product could be improved by using a soft, compressible material either inside or outside of the cellulosic barrier layer as shown in the examples shown in FIG. 5.

In FIG. 5, the Cairpad® and poly versions were tested as reference points for the cellulosic barrier layer prototypes. The Cairpad bedpad is a commercially available bedpad that is designed for air-flow therapy beds, and is produced by Attends. The poly version utilized a commercially available MicroP "breathable" microporous poly film, similar to the one tested for TABLE 2, as a barrier layer in combination with a 42 gsm nonwoven backsheet. Prototype 1 used a three-layer prototype similar to laminate 10b of FIG. 1C that included a 10 gsm spunbond nonwoven stabilization layer like layer 30 of FIG. 1C, a 17 gsm creped tissue barrier layer like layer 14 of FIG. 1C, and a 42 gsm sponbond nonwoven support layer like layer 18 of FIG. 1C. Prototype 2 used a three-layer prototype similar to laminate 10b of FIG. 1C that included a 10 gsm spunbond nonwoven stabilization layer like layer 30 of FIG. 1C, a 36 gsm creped paper barrier layer like layer 14 of FIG. 1C, and a 42 gsm spunbond nonwoven support layer like layer 18 of FIG. 1C.

Additional tests were performed on the 10/17/42 prototype laminate beneath an untreated topsheet—not including an absorbent core—both with and without a compressible layer beneath the laminate, the results of which are shown in TABLE 10. The untreated topsheet included a 12 gsm hydrophobic SSS spunbond nonwoven manufactured by Fitesa in Simpsonville, S.C. The compressible layer included two layers of 50 gsm high-loft through-air bonded nonwoven, specifically ATB NW Vortex 50 gsm, manufactured by Texsus SpA in Pistoia, Italy. In these tests, the sheet of compressible material was large enough to span the entire column of liquid applied during the test. The pinhole testing for Table 10 was completed using the Liquid-Column Pinhole (Hard-Hard) Test Method defined in Section F entitled "Liquid-Column Pinhole Test Method."

TABLE 10

Compressible layer and effect on performance

| Layers | Hydrohead (mm $H_2O$) | Pinhole Performance using Liquid-Column Pinhole (Hard/Hard) Test Method | | | |
|---|---|---|---|---|---|
| | | 400 mm $H_2O$ | 600 mm $H_2O$ | 800 mm $H_2O$ | 1000 mm $H_2O$ |
| untreated topsheet, over 10/17/42 laminate | 202 | 0 | 0 | CS | |
| untreated topsheet, over 10/17/42 laminate, over compressible layer | 260 | 0 | 0 | 0 | 0 |

The additional compressible layer has been shown to be particularly effective at improving pinhole performance, and it can maintain sufficient free volume under pressure, such as in the range of 400 to 800 mm $H_2O$, for in-plane spreading of liquid expressed from the core. The additional compressible layer is currently believed to effectively limit the amount of pressure that can be generated within the absorbent core to force liquid through the breathable backsheet. In the tests reflected in Table 10, the placement of the compressible layer beneath the nonwoven support layer of the 10/17/42 laminate was a function of the laminate being formed and available rather than any requirement that the compressible layer be disposed beneath the nonwoven support layer. Rather, in some embodiments of the present laminates, the compressible layer may instead be disposed between the support layer and the cellulosic barrier layer.

FIGS. 7A and 7B depict an example of an absorbent article 200a that includes such an additional compressible layer 216 that comprises a sheet of material that has a thickness and is compressible in a direction of its thickness, left and right in the plane of the page in FIG. 7B. Compressible layer 216 may comprise, for example, one or more of an apertured film, a lofty through-air-bonded nonwoven, a second cellulosic fiber layer, and/or another compressible material. When the compressible layer includes a second cellulosic fiber layer, the second cellulosic fiber layer can be creped. This additional compressible layer can also be effective when the compressible layer is not coextensive with the core, such as, for example, when only a small patch of the compressible material is disposed under or near the center of an absorbent core. For example, as shown in FIG. 7A, compressible layer 216 spans only a portion of laminate 10 and only a portion of topsheet 204. In this embodiment, compressible layer 216 is disposed in a position below where urine is expected to most often be introduced to the topsheet such that the compressible layer is located in a position at which liquid is expected to reach the barrier layer at the highest rate during use. In other embodiments, the compressible layer is coextensive with the barrier layer, with the core, and/or with the topsheet. While compressible layer 216 is not labeled as a component of laminate 10, the compressible layer may be formed as a component of the present laminates, for example, bonded to or above barrier layer 14 prior to manufacture of an absorbent article, or may be added during manufacture of the absorbent article.

2. Additional Spacer Layer and/or Support Layer Characteristics

In some of the present laminates, a support layer like layer 18 of FIG. 1A is disposed outside of a cellulosic barrier layer 14, 14a. In such embodiments, the support layer can comprise a nonwoven with a hydrostatic head in the range of 200 to 300 mm $H_2O$. While this may be lower than the hydrohead of the barrier layer, the combination of such a support layer with the barrier layer has been found to improve pinhole performance of the barrier layer. This is believed to do so by minimizing the effect of point defects in the barrier layer by supporting the regions surrounding the point defects.

In some embodiments, such as laminate 100 of FIG. 2, a spacer layer 34 is also disposed between cellulosic barrier layer 14 and support layer (e.g., 18). In this configuration, the spacer layer comprises a material with voids or interstices in at least a surface of the spacer layer that faces the barrier layer to provide a free volume for accommodating liquid passing through point defects or pinholes in the cellulosic barrier layer. Such voids or interstices need not pass through the entire thickness of the spacer layer. Such a spacer layer can permit a small volume of escaped liquid to be present in the spacer layer at pressure low enough to be contained effectively by a conventional nonwoven, such as an SMS nonwoven, with a hydrohead in the range of only 200 to 300 mm $H_2O$. For example, support layer 18 can comprise a nonwoven with such a hydrohead value. In some embodiments, such spacer layers not only provide free volume that can receive liquid, but also provide some resistance to the flow of liquid through the material so as to provide a pressure drop across the spacer layer, for example, to reduce 600 mm $H_2O$ applied to the upper side of the barrier layer to 400 mm $H_2O$ at the lower side of the spacer layer. Examples of suitable spacer layers include apertured films, through-air bonded nonwovens, other nonwovens with relatively lower densities, and/or other materials that include or define voids that can receive liquid in the manner described.

3. Multi-sheet Cellulosic Barrier Layer

In some of the present embodiments, like laminate 10a of FIG. 1B, the cellulosic barrier layer comprises two sheets, for example sheets 26, of cellulosic fiber material. In such embodiments, each of the two sheets can have a relatively low basis weight, such as, for example, 17 gsm. If individual sheets of cellulosic fiber material each possess a sufficiently small pore size distribution to generate high hydrohead but have too many defects for good pinhole performance, two or more layers coupled together can provide a pinhole-free cellulosic barrier layer by reducing the likelihood that any one defect in one sheet will be aligned with a defect in another sheet. These two or more layers can, for example, be bonded together via an adhesive, such as a filamentary adhesive. Laminates were incorporated into prototype bedpads and then samples removed from the bedpads and stacked in the configurations described in Table 11. As shown in Table 11, a laminate containing a two-sheet cellulosic barrier layer (17 gsm-17 gsm) was particularly effective at reducing pinhole defects currently believed to be associated with damage caused during assembly of the layers into an absorbent article such as the prototype bedpad.

TABLE 11

Laminate layer combinations and effect on performance

| Prototype Layers | Hydrohead (mm $H_2O$) | Pinhole Performance using Liquid-Column Pinhole (Hard/Hard) Test Method | | |
|---|---|---|---|---|
| | | 400 mm $H_2O$ | 600 mm $H_2O$ | 800 mm $H_2O$ |
| untreated topsheet, over single-sheet barrier layer 10/17/42 laminate after assembly into and removal from bedpad | 177 | CS | | |
| untreated topsheet, over two-sheet barrier layer 10/17-17/42 laminate after assembly into and removal from bedpad | 367 | 0 | 3P | CS |

4. Surfactant-Free Construction

The effectiveness of the present cellulosic fiber layers can be further improved in absorbent articles that are configured to not reduce the surface tension of liquid like saline or urine as it passes through the absorbent article to the barrier layer. Finishes used to make olefinic nonwoven topsheets, as well as nonwoven or film ADLs, hydrophilic are generally semi-durable, surface active materials that can be washed from the materials by urine during use of an absorbent product, and that can lower the surface tension of the urine. Urine with a reduced surface tension can reduce the effective pinhole performance of a breathable backsheet, at least because the reduced surface tension reduces resistance to flow through pinholes. Liquids of low surface tension can be forced more easily through a hydrophobic cellulosic barrier layer at reduced pressures. As a result, absorbent articles with the present cellulosic barrier layers will typically exhibit improved liquid barrier performance when the topsheets and ADLs of such articles do not include non-durable or semi-durable surfactants. For example, some embodiments of the present absorbent articles do not include non-durable surfactants and/or semi-durable surfactants on one or more of: the topsheet, the ADL if included, the spacer layer if included, or the compressible layer if included. In such embodiments, one or more of: the topsheet, the ADL if included, the spacer layer if included, or the compressible layer if included, can comprise a durable finish, or a finish with hydrophilic material of relatively low surface activity.

Additional tests were performed on the 10/17/42 prototype laminate beneath an untreated topsheet—not including an absorbent core—and beneath topsheets of various treatments, the results of which are shown in TABLE 12. The untreated topsheet included a 12 gsm hydrophobic SSS spunbond nonwoven manufactured by Fitesa. The topsheet for prototype No. 4 in Table 12 was a 12 gsm hydrophilic SSS spunbond nonwoven also manufactured by Fitesa, and finished using Lertisan HD 20/3 manufactured by Zschimmer and Schwartz in Lahnstein, Germany at an add on level of 0.003-0.005 grams per gram of nonwoven. The topsheet for prototype No. 5 in Table 12 was also a 12 gsm hydrophilic SSS spunbond nonwoven manufactured by Fitesa, but was finished using a solution of Clarisoy 100 manufactured by Archer Daniels Midland in Decatur, Ill. at an add on level of 0.012 grams per gram of nonwoven. In these tests, the spacer layer was large enough to span the entire column of liquid applied during the test. The pinhole testing for Table 12 was completed using the Liquid-Column Pinhole (Hard-Hard) Test Method defined in Section F entitled "Liquid-Column Pinhole Test Method."

TABLE 12

Examples of topsheet/core treatments and effect on performance

| Prototype Layers | Hydrohead (mm $H_2O$) | Pinhole Performance using Liquid-Column Pinhole (Hard-Hard) Test Method | | |
|---|---|---|---|---|
| | | 400 mm $H_2O$ | 600 mm $H_2O$ | 800 mm $H_2O$ |
| 10/17/42 laminate, below untreated topsheet | 202 | 0 | 0 | CS |
| 10/17/42 laminate, below topsheet treated with HD 20/3 | 198 | CS | | |
| 10/17/42 laminate, below topsheet treated with Clarisoy 100 | 180 | 0 | CS | |

E. Pinhole Test Method

This Pinhole Test Method is one of the ways that the integrity of a material can be tested and compared to other materials. This Pinhole Test Method simulates a backsheet beneath a wet core that is under the pressure of a human body which can impart varying forces.

The Pinhole Test Method utilizes the following equipment and components:

a. a tap water-alcohol solution that is 5% isopropanol by weight, and has a surface tension of 50±3 mN/m at a temperature of 22° C.;

b. a flat polycarbonate plate with a length of 220 mm, a width of 100 mm, a thickness of 11 mm, and rounded edges around the perimeter of its two largest surfaces;

c. a sample of the product to be tested with a length of 300 mm and a width of 175 mm;

d. a soft foam rubber pad that has a length of 350 mm and a width of 310 mm, has a compression modulus of 7000±500 Pa, and is wrapped in a poly film;

e. rectangular pieces of paper towel each with a length of 200 mm and a width of 75 mm;

f. a piece of tissue paper with a length of at least 300 mm and a width of at least 175 mm;

g. weights simulating 400 mm, 600 mm, and 800 mm of water head, each having a lower surface with a length of 305 mm and a width of 305 mm;

h. a timer; and
i. a tray that is large enough to soak the paper towel with the water-alcohol solution.

The Pinhole Test Method proceeds with the following steps in the listed order:
  a. The foam pad is placed on a flat, level surface such as a benchtop.
  b. The tissue paper is centered on top of the foam pad.
  c. The product sample to be tested is placed is centered on top of the tissue paper.
  d. A piece of paper towel is soaked in the water-alcohol solution.
  e. The paper towel is lifted from the tray and excess solution allowed to drip from the paper towel until the drip rate slows to 5 seconds between drops.
  f. The wet paper towel is centered on top of the product sample to be tested.
  g. The flat polycarbonate plate is placed is centered on top of the wet paper towel.
  h. The appropriate water head weight is centered on top of the plate and the timer set for ten minutes.
  i. Once the time expires, the weight is lifted off the product sample.
  j. The paper towel, polycarbonate plate, and product sample are lifted off the tissue while maintaining the position of the paper towel centered relative to the product sample.
  k. The number of wet spots on the tissue, indicating the number of pinholes in the product sample, is counted and the results recorded.

If the tissue becomes completely saturated, that result ("CS") is recorded but the process is terminated for the sample and not continued on to the higher weight(s). Steps a.-k. are first completed using the 400 mm water head weight, and then are repeated for each of the 600 mm water head and 800 mm water head weights, using a new product sample for each weight.

F. Liquid-Column Pinhole Test Method

This Liquid-Column Pinhole (Soft-Hard) Test Method and the Liquid-Column Pinhole (Hard-Hard) Test Method are additional ways that the integrity of a material can be tested and compared to other materials. These Liquid-Column Pinhole Test Methods simulate a backsheet beneath a wet core that is under the pressure of a human body which can impart varying forces.

The Liquid-Column Pinhole (Soft-Hard) Test Method utilizes the following equipment and components:
  a. a tap water-alcohol solution that is 5% isopropanol by weight, and has a surface tension of 50±3 mN/m at a temperature of 22° C.;
  b. a hard neoprene rubber pad with a length of 305 mm and a width of 305 mm, and a Shore A hardness of 30±3;
  c. a sample of the product to be tested with a length of 150 mm, a width of 150 mm, and a thickness of 11 mm;
  d. two circular pieces of paper towel each with a diameter of 75 mm;
  e. a piece of low-porosity tissue paper with a length of at least 160 mm and a width of at least 160 mm;
  f. a container of tap water;
  g. a timer;
  h. a small tray that is large enough to soak the paper towel pieces with the water-alcohol solution;
  i. a lab jack;
  j. two ring stands;
  k. a hydrohead tube with a nominal length of 120 cm (4 feet), and an inner diameter of 10.5 cm;
  l. a flexible rubber bladder, such as from a large rubber glove, that is elastic and has sufficient tensile strength to support a 1000 mm column of water and sufficient elasticity to distend 3.25±0.3 mm from the center of the hydrohead tube for each 100 mm of water pressure over a range of 200-600 mm water pressure;
  m. a hose clamp large enough to fit around the hydrohead tube to secure the rubber bladder to an end of the hydrohead tube;
  n. a pump and tubing of sufficient length to extend from the container to the hydrohead tube; and
  o. two tube clamps; and
  p. two large rubber bands.

The Liquid-Column Pinhole (Soft-Hard) Test Method proceeds with the following steps in the listed order:
  a. The ring stands are placed on a flat surface such that they are parallel to each other.
  b. The tube clamps are, respectively, attached onto the very tops of each ring stand.
  c. The first rubber band is placed around the rim of the hydrohead tube. The rubber bladder is then placed over the tube end, ensuring a snug fit with no wrinkles, and the second rubber band is then placed around the outside of the rubber bladder at the edge of the rim of the tube. The hose clamp is then tightened around the rubber bands, rubber bladder, and rim.
  d. The hydrohead tube, bladder side down, is positioned into the hose clamps with 20 cm of clearance between the bottom of the hydrohead tube and the top of the ring stand base.
  e. Alcohol solution is poured into the small try in sufficient quantity to permit the paper towel pieces to be completely submerged. Two pieces of paper towel are layered one on top of the other, and submerged in the solution until they are completely saturated. The paper towel pieces are then lifted from the tray and excess solution allowed to drip from the paper towel pieces until the drip rate slows to 5 seconds between drops.
  f. The hard rubber pad is centered on top of the fully lowered lab jack, the tissue is centered on top of the hard rubber pad, the product sample is centered on top of the tissue with the wet or body-facing side (if any) of the product sample facing up, and the saturated paper towel pieces are centered on top of top of the product sample.
  g. The lab jack—with hard rubber pad, tissue, product sample, and paper towel pieces—is placed directly beneath the hydrohead tube assembly with the sample and paper towel centered beneath the tube.
  h. The lab jack is raised until the uppermost paper towel piece is 1-2 mm below the rim of the hydrohead tube. To avoid pinch points, the uppermost paper towel piece and hydrohead tube should not be touching.
  i. The pump and tubes are then used to transfer tap water from the container to the hydrohead tube to a level of 400 mm in the hydrohead tube, at a flowrate sufficient to increase the height of the column of liquid in the hydrohead tube at a rate of 100 mm per second.
  j. The timer is set to 10 minutes.
  k. Once the time expires, the lab jack is lowered, and the paper towel pieces and product sample are lifted off the tissue while maintaining the position of the paper towel pieces centered relative to the product sample.

l. The number of wet spots on the tissue, indicating the number of pinholes in the product sample, is counted and the results recorded.

If when counting the tissue is completely saturated, that result ("CS") is recorded but the process is terminated for the sample and not continued on to the higher weight(s). Steps a.-l. are first completed using the 400 mm of water in the hydrohead tube and then, if there are no pinholes in step l., the product sample and paper towel pieces are placed back on the tissue centered relative to each other and to the hard rubber pad, and steps h.-l. are repeated for each of 600 mm, 800 mm, and 1000 mm water levels in the hydrohead tube. For heights greater than 600 mm, the water level in the hydrohead is lowered to 600 mm or less before lowering the lab jack and removing the product sample and paper towel pieces to count pinholes.

The Liquid-Column Pinhole (Hard-Hard) Test Method utilizes the same equipment and components as the Liquid-Column Pinhole (Soft-Hard) Test Method, with the following exceptions:

a. a polycarbonate plate having a length of 150 mm and a width of 150 mm is used instead of the hard neoprene rubber pad;
b. a circular glass frit with a diameter of 120 mm; and
c. a plastic sheet or poly film having a length of at least 150 mm and a width of at least 150 mm.

The Liquid-Column Pinhole (Hard-Hard) Test Method proceeds with the following steps in the listed order:

a. The ring stands are placed on a flat surface such that they are parallel to each other.
b. The tube clamps are, respectively, attached onto the very tops of each ring stand.
c. The first rubber band is placed around the rim of the hydrohead tube. The rubber bladder is then placed over the tube end, ensuring a snug fit with no wrinkles, and the second rubber band is then placed around the outside of the rubber bladder at the edge of the rim of the tube. The hose clamp is then tightened around the rubber bands, rubber bladder, and rim.
d. The hydrohead tube, bladder side down, is positioned into the hose clamps with 20 cm of clearance between the bottom of the hydrohead tube and the top of the ring stand base.
e. Alcohol solution is poured into the small try in sufficient quantity to permit the paper towel pieces to be completely submerged. Two pieces of paper towel are layered one on top of the other, and submerged in the solution until they are completely saturated. The paper towel pieces are then lifted from the tray and excess solution allowed to drip from the paper towel pieces until the drip rate slows to 5 seconds between drops.
f. The polycarbonate plate is centered on top of the fully lowered lab jack, the tissue is centered on top of the polycarbonate plate, the product sample is centered on top of the tissue with the wet or body-facing side (if any) of the product sample facing up, the saturated paper towel pieces are centered on top of the product sample, the plastic sheet is centered on top of the paper towel pieces, and the glass frit is centered on top of the plastic sheet.
g. The lab jack—with polycarbonate plate, tissue, product sample, and paper towel pieces—is placed directly beneath the hydrohead tube assembly with the sample and paper towel centered beneath the tube.
h. The lab jack is raised until the glass frit is 1-2 mm below the rim of the hydrohead tube. To avoid pinch points, the glass frit and hydrohead tube should not be touching.
i. The pump and tubes are then used to transfer tap water from the container to the hydrohead tube to a level of 400 mm in the hydrohead tube, at a flowrate sufficient to increase the height of the column of liquid in the hydrohead tube at a rate of 100 mm per second.
j. The timer is set to 10 minutes.
k. Once the time expires, the lab jack is lowered, and the paper towel pieces, product sample, plastic sheet, and glass frit are lifted off the tissue while maintaining the position of the paper towel pieces, plastic sheet, and glass frit centered relative to the product sample.
l. The number of wet spots on the tissue, indicating the number of pinholes in the product sample, is counted and the results recorded.

If when counting the tissue is completely saturated, that result ("CS") is recorded but the process is terminated for the sample and not continued on to the higher weight(s). Steps a.-l. are first completed using the 400 mm of water in the hydrohead tube and, if there are no pinholes in step l., the product sample, paper towel pieces, plastic sheet, and glass frit are then placed back on the tissue centered relative to each other and to the polycarbonate plate, and steps h.-l. are repeated for each of 600 mm, 800 mm, and 1000 mm water levels in the hydrohead tube. For heights greater than 600 mm, the water level in the hydrohead is lowered to 600 mm or less before lowering the lab jack and removing the product sample, paper towel pieces, plastic sheet, and glass frit to count pinholes.

G. Modified Pinhole Test Method

This Modified Pinhole Test Method is one of the ways that the integrity of a material can be tested and compared to other materials. This Modified Pinhole Test Method simulates a backsheet beneath a wet core that is under the pressure of a human body which can impart varying forces.

The Modified Pinhole Test Method utilizes the following equipment and components:

a. a tap water-alcohol solution that is 5% isopropanol by weight, and has a surface tension of 50±3 mN/m at a temperature of 22° C.;
b. a flat polycarbonate plate with a length of 220 mm, a width of 100 mm, a thickness of 11 mm, and rounded edges around the perimeter of its two largest surfaces;
c. a sample of the product to be tested with a length of 300 mm and a width of 175 mm;
d. a large soft foam rubber pad that has a length of 350 mm and a width of 310 mm, has a compression modulus of 7000±500 Pa, and is wrapped in a poly film;
e. a small soft foam rubber pad that has a length of 100 mm and a width of 225 mm, has a compression modulus of 7000±500 Pa, and is wrapped in a poly film;
f. two hard neoprene rubber pads each with a length of 305 mm and a width of 305 mm, and a Shore A hardness of 30±3;
g. rectangular pieces of paper towel each with a length of 200 mm and a width of 75 mm;
h. a piece of tissue paper with a length of at least 300 mm and a width of at least 175 mm;

i. weights simulating 400 mm, 600 mm, and 800 mm of water head, each having a lower surface with a length of 305 mm and a width of 305 mm;
j. a timer; and
k. a tray that is large enough to soak the paper towel with the water-alcohol solution.

The Modified Pinhole (Soft-Soft) Test Method proceeds with the following steps in the listed order:
a. The large foam rubber pad, wrapped in poly film, is placed on a flat, level surface such as a benchtop.
b. The tissue paper is centered on top of the foam pad.
c. The product sample to be tested is centered on top of the tissue paper.
d. A piece of paper towel is soaked in the water-alcohol solution.
e. The paper towel is lifted from the tray and excess solution allowed to drip from the paper towel until the drip rate slows to 5 seconds between drops.
f. The wet paper towel is centered on top of the product sample to be tested.
g. The small foam rubber pad, wrapped in poly film, is placed is centered on top of the wet paper towel.
h. The flat polycarbonate plate is placed is centered on top of the small foam rubber pad.
i. The appropriate water head weight is centered on top of the polycarbonate plate and the timer set for ten minutes.
j. Once the time expires, the weight is lifted off the product sample.
k. The paper towel, small foam rubber pad, polycarbonate plate, and product sample are lifted off the tissue.
l. The number of wet spots on the tissue, indicating the number of pinholes in the product sample, is counted and the results recorded.

If the tissue becomes completely saturated, that result ("CS") is recorded but the process is terminated for the sample and not continued on to the higher weight(s). Steps a.-l. are first completed using the 400 mm water head weight, and then are repeated for each of the 600 mm water head and 800 mm water head weights, using a new product sample for each weight.

The Modified Pinhole (Soft-Hard) Test Method proceeds with the following steps in the listed order:
a. A first one of the hard neoprene rubber pads is placed on a flat, level surface such as a benchtop.
b. The tissue paper is centered on top of the first hard neoprene rubber pad.
c. The product sample to be tested is centered on top of the tissue paper.
d. A piece of paper towel is soaked in the water-alcohol solution.
e. The paper towel is lifted from the tray and excess solution allowed to drip from the paper towel until the drip rate slows to between 5 seconds between drops.
f. The wet paper towel is centered on top of the product sample to be tested.
g. The small foam rubber pad, wrapped in poly film, is centered on top of the wet paper towel.
h. The flat polycarbonate plate is centered on top of the small foam rubber pad.
i. The appropriate water head weight is centered on top of the polycarbonate plate and the timer set for ten minutes.
j. Once the time expires, the weight is lifted off the product sample.
k. The paper towel, small foam rubber pad, polycarbonate plate, and product sample are lifted off the tissue.
l. The number of wet spots on the tissue, indicating the number of pinholes in the product sample, is counted and the results recorded.

If the tissue becomes completely saturated, that result ("CS") is recorded but the process is terminated for the sample and not continued on to the higher weight(s). Steps a.-l. are first completed using the 400 mm water head weight, and then are repeated for each of the 600 mm water head and 800 mm water head weights, using a new product sample for each weight.

The Modified Pinhole (Hard-Hard) Test Method proceeds with the following steps in the listed order:
a. One of the hard neoprene rubber pads is placed on a flat, level surface such as a benchtop.
b. The tissue paper is centered on top of the first hard neoprene rubber pad.
c. The product sample to be tested is centered on top of the tissue paper.
d. A piece of paper towel is soaked in the water-alcohol solution.
e. The paper towel is lifted from the tray and excess solution allowed to drip from the paper towel until the drip rate slows to 5 seconds between drops.
f. The wet paper towel is centered on top of the product sample to be tested.
g. The second hard neoprene rubber pad is centered on top of the wet paper towel.
h. The flat polycarbonate plate is centered on top of the second hard neoprene rubber pad.
i. The appropriate water head weight is centered on top of the plate and the timer set for ten minutes.
j. Once the time expires, the weight is lifted off the product sample.
k. The paper towel, second hard neoprene rubber pad, polycarbonate plate, and product sample are lifted off the tissue.
l. The number of wet spots on the tissue, indicating the number of pinholes in the product sample, is counted and the results recorded.

If the tissue becomes completely saturated, that result ("CS") is recorded but the process is terminated for the sample and not continued on to the higher weight(s). Steps a.-l. are first completed using the 400 mm water head weight, and then are repeated for each of the 600 mm water head and 800 mm water head weights, using a new product sample for each weight.

H. Air Permeability Test Method

For purposes of this disclosure, air permeability is measured as Frazier air permeability using ASTM D737-04, "Standard Method for Air Permeability of Textile Fabrics," which standard is incorporated by reference in its entirety. This test method is used to determine the rate of air flow passing perpendicularly through a known area under a prescribed air pressure differential between the two surfaces of planar material. This test method proceeds with the following steps in the listed order:
a. A product sample preconditioned by placing it for at least 4 hours before testing in an environment with a temperature of 71±2° F. and relative humidity of 65±2%.
b. The product sample is disposed over the test head of a commercially available air permeability testing machine such that that product sample is secured over the test head with a clamp and/or seal that minimizes edge leakage.

c. The test machine is turned on to steadily draw air through and perpendicular to the product sample at a pressure drop of 125 Pa across the product sample.
d. The air permeability of the product sample is read from the testing machine or measured with flowmeter.

I. Hydrostatic Head Test Method

For purposes of this disclosure, hydrostatic head—which may also be referred to as "hydrohead" or "HH"—is measured using AATCC Test Method 127-2008, "Water Resistance: Hydrostatic Pressure Test," which standard is incorporated by reference in its entirety. This test method proceeds with the following steps in the listed order:
a. The product to be tested is preconditioned by placing it for at least 4 hours before testing in an environment with a temperature of 71±2° F. and relative humidity of 65±2%.
b. A product sample with a width of 200 mm and a length of 200 mm is secured to a a commercially available hydrostatic head tester, as appropriate for the particular tester. For example, for hydrohead tube having a nominal length of 1200 mm and an inner diameter of 10.5 cm, the product sample can be secured over a lower end of the tube via two rubber bands and a hose clamp in the manner described in Section F.
c. Water is added above the sample, for example to a hydrohead tube, at a rate of 10 mm per second until three (3) drops of water penetrate through and drip below the sample, at which point the height of the water column is recorded.

J. Percent Elongation Test Method

Percent elongation or % elongation, for purposes of this disclosure, is measured using the TAPPI/ANSI Standard T-494 om-13 entitled "Tensile properties of paper and paperboard (using constant rate of elongation apparatus)," which standard is incorporated by reference in its entirety. This test method proceeds with the following steps in the listed order:
a. A product sample with a width of 25±1 mm and length great enough to be clamped in line-contact clamping jaws of a commercially available tensile testing machine with a test span of 180±5 mm. The length of the sample may, for example, be 230 mm. Line-contacting jaws are those that clamp a sample between a flat surface and a cylindrical surface, or between two cylindrical surfaces. The respective lines of contact of the jaws are parallel to each other within an angle of ±1° and do not change more than 0.5° during elongation of the sample, and are also perpendicular to the direction of elongation or stretch within an angle of ±1°.
b. The product sample is clamped between the line-contact clamping jaws of the commercially available tensile testing machine with a clamping force sufficient to resist slippage of the product sample relative to the jaws during testing. The product sample is clamped with a test span of 180±5 mm such that the product sample does not have any noticeable slack but is not strained while clamping.
c. The jaws are separated to elongate the product sample at a rate of 25 mm per minute until the product sample breaks.
d. The percent elongation, or change in length relative to starting length, is read from the tensile testing machine and recorded.

The above specification and examples provide a complete description of the structure and use of illustrative embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the methods and systems are not intended to be limited to the particular forms disclosed. Rather, they include all modifications and alternatives falling within the scope of the claims, and embodiments other than the one shown may include some or all of the features of the depicted embodiment. For example, elements may be omitted or combined as a unitary structure, and/or connections may be substituted. By way of further example, while the claims may specify a specifies value of pinhole performance to be obtained with a particular pinhole testing method, other embodiments of the claimed layers, laminates, or articles can have the claimed values for pinhole-free performance under any one of the other pinhole test methods described in this disclosure. Further, where appropriate, aspects of any of the examples described above may be combined with aspects of any of the other examples described to form further examples having comparable or different properties and/or functions, and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. A breathable backsheet assembly comprising:
a cellulosic fiber barrier layer having a hydrophobic sizing, the barrier layer comprising sheets of wetlaid tissue or wetlaid paper, the barrier layer having an air permeability of more than 0.5 ft$^3$/min-ft$^2$ and being able to hold a hydrostatic head of more than 200 mm H$_2$O, the barrier layer comprising two sheets of cellulosic fiber material, each sheet having a basis weight of between 15 grams per square meter (gsm) and 20 gsm; and
a support layer positioned beneath and coupled to the barrier layer, the support layer comprising a nonwoven fabric;
where the barrier layer and the support layer define a laminate.

2. The breathable backsheet assembly of claim 1, where the laminate is able to remain pinhole free at 400 mm H$_2$O for 10 minutes using the Liquid-Column Pinhole (Soft-Hard) Test Method.

3. The breathable backsheet assembly of claim 1, where the barrier layer comprises two sheets of tissue or paper bonded together.

4. The breathable backsheet assembly of claim 1, where the barrier layer is creped.

5. The breathable backsheet assembly of claim 4, where the barrier layer has a percent elongation of between 5% and 55%.

6. The breathable backsheet assembly of claim 1, where the barrier layer is bonded to the support layer by a filamentary adhesive or thermal bonds.

7. The breathable backsheet assembly of claim 1, where the support layer has a basis weight of no more than 20 gsm.

8. The breathable backsheet assembly of claim 7, where the support layer comprises a spunbond-meltblown-spunbond (SMS) nonwoven able to hold a hydrostatic head of more than 150 mm H$_2$O.

9. A disposable absorbent article, comprising;
a breathable backsheet assembly of claim 1;
a liquid-permeable topsheet; and
an absorbent core positioned between the topsheet and the breathable backsheet assembly, the absorbent core comprising cellulosic fibrous material and/or superabsorbent polymeric (SAP) particles;
where the breathable backsheet assembly is coupled to the topsheet.

10. The disposable absorbent article of claim 9, where the disposable absorbent article does not substantially reduce the surface tension of saline or urine passing through the topsheet to the barrier layer.

11. The disposable absorbent article of claim 10, comprising:
an acquisition-distribution layer (ADL) disposed between the absorbent core and the topsheet, the ADL not substantially reducing the surface tension of saline or urine passing through the ADL to the barrier layer.

12. The disposable absorbent article of claim 9, where the breathable backsheet assembly further comprises:
a compressible layer comprising a sheet of material having a thickness and that is compressible in a direction of the thickness;
where the compressible layer is disposed between the barrier layer and the absorbent core, or between the barrier layer and the support layer.

13. The disposable absorbent article of claim 12, where the compressible layer is not coextensive with the breathable backsheet assembly.

14. The disposable absorbent article of claim 9, where the disposable absorbent article comprises an incontinence brief, the barrier layer has an air permeability of more than 0.5 ft$^3$/min-ft$^2$ and is able to hold a hydrostatic head of more than 600 mm H$_2$O, and the laminate remaining pinhole free at 800 mm H$_2$O for 10 minutes using the Liquid-Column Pinhole (Soft-Hard) Test Method.

15. The disposable absorbent article of claim 9, where the disposable absorbent article comprises a pull-up underwear or a bladder control pad, the barrier layer has an air permeability of more than 1.5 ft$^3$/min-ft$^2$ and is able to hold a hydrostatic head of more than 400 mm H$_2$O, and the laminate remaining pinhole free at 600 mm H$_2$O for 10 minutes using the Liquid-Column Pinhole (Soft-Hard) Test Method.

16. The disposable absorbent article of claim 9, where the disposable absorbent article comprises a bedpad, the barrier layer has an air permeability of more than 1.5 ft$^3$/min-ft$^2$ and holding a hydrostatic head of more than 400 mm H$_2$O, and the laminate remaining pinhole free at 400 mm H$_2$O for 10 minutes using the Liquid-Column Pinhole (Soft-Hard) Test Method.

17. The disposable absorbent article of claim 9, further comprising:
a spacer layer disposed between the barrier layer and the support layer, the spacer layer including a plurality of voids or interstices in at least a surface of the spacer layer that faces the barrier layer.

18. The disposable absorbent article of claim 17, where the spacer layer is not coextensive with the breathable backsheet assembly.

19. A method of making a disposable absorbent product, the method comprising:
providing a liquid permeable topsheet, an absorbent core, a nonwoven support layer, and a cellulosic fiber barrier layer having a hydrophobic sizing, the barrier layer comprising sheets of wetlaid tissue or wetlaid paper, the barrier layer comprising two sheets of cellulosic fiber material, each sheet having a basis weight of between 15 grams per square meter (gsm) and 20 gsm; and
coupling the topsheet, the barrier layer, and support layer together such that the absorbent core is retained between the topsheet and the barrier layer, and the barrier layer is retained between the absorbent core and the support layer.

20. The method of claim 19, further comprising:
providing an acquisition-distribution layer (ADL); and
coupling the ADL to the topsheet such that the ADL is retained between the topsheet and the absorbent core.

21. The method of claim 20, where the topsheet and the ADL do not substantially reduce the surface tension of saline or urine passing through the topsheet and the ADL to the barrier layer.

* * * * *